US009168082B2

(12) United States Patent
Evans et al.

(10) Patent No.: US 9,168,082 B2
(45) Date of Patent: Oct. 27, 2015

(54) FINE DISSECTION ELECTROSURGICAL DEVICE

(75) Inventors: Doug Evans, Austin, TX (US); Michael D. Foster, Palo Alto, CA (US); Philip M. Tetzlaff, Austin, TX (US); Rajitha Aluru, Austin, TX (US); Jean Woloszko, Austin, TX (US); Johnson E. Goode, Austin, TX (US)

(73) Assignee: ArthroCare Corporation, Austin, TX (US)

( * ) Notice: Subject to any disclaimer, the term of this patent is extended or adjusted under 35 U.S.C. 154(b) by 1286 days.

(21) Appl. No.: 13/023,603

(22) Filed: Feb. 9, 2011

(65) Prior Publication Data

US 2012/0203219 A1    Aug. 9, 2012

(51) Int. Cl.
| | |
|---|---|
| *A61B 18/18* | (2006.01) |
| *A61B 18/04* | (2006.01) |
| *A61B 18/00* | (2006.01) |
| *A61B 18/14* | (2006.01) |

(52) U.S. Cl.
CPC ..... *A61B 18/042* (2013.01); *A61B 2018/00583* (2013.01); *A61B 2018/00589* (2013.01); *A61B 2018/1472* (2013.01); *A61B 2218/002* (2013.01)

(58) Field of Classification Search
CPC ................... A61B 18/042; A61B 2018/00583; A61B 2218/002; A61B 2018/1472; A61B 2018/00589
USPC ..................................................... 606/38–45
See application file for complete search history.

(56) References Cited

U.S. PATENT DOCUMENTS

| | | | |
|---|---|---|---|
| 2,050,904 A | 8/1936 | Talley | 219/233 |
| 2,056,377 A | 10/1939 | Wappler | 125/303 |
| 3,633,425 A | 1/1972 | Sanford | 73/356 |
| 3,815,604 A | 6/1974 | O'Malley et al. | 128/305 |
| 3,828,780 A | 8/1974 | Morrison, Jr. et al. | 128/275 |
| 3,901,242 A | 8/1975 | Storz | 128/303 |
| 3,920,021 A | 11/1975 | Hiltebrandt | 128/303 |
| 3,939,839 A | 2/1976 | Curtiss | 128/303 |
| 3,970,088 A | 7/1976 | Morrison | 128/303 |

(Continued)

FOREIGN PATENT DOCUMENTS

| | | | |
|---|---|---|---|
| DE | 3930451 A1 | 3/1991 | A61B 17/39 |
| DE | 202014002299.20 | 7/2014 | A61B 18/12 |

(Continued)

OTHER PUBLICATIONS

Barry et al., "The Effect of Radiofrequency-generated Thermal Energy on the Mechanical and Histologic Characteristics of the Arterial Wall in Vivo: Implications of Radiofrequency Angioplasty" *American Heart Journal* vol. 117, pp. 332-341, 1982.

(Continued)

*Primary Examiner* — Joseph Stoklosa
*Assistant Examiner* — Amanda Zink
(74) *Attorney, Agent, or Firm* — David A. Warmbold

(57) ABSTRACT

An electrosurgical wand. At least some of the illustrative embodiments are electrosurgical wands including an elongate shaft that defines a handle end and a distal end, a first discharge aperture on the distal end of the elongate shaft, a first active electrode of conductive material disposed on the distal end of the elongate shaft, the first active electrode has an edge feature, a first return electrode of conductive material disposed a substantially constant distance from the first active electrode, and an aspiration aperture on the distal end of the elongate shaft fluidly coupled to a second fluid conduit.

37 Claims, 9 Drawing Sheets

(56) References Cited

U.S. PATENT DOCUMENTS

| | | | |
|---|---|---|---|
| 4,033,351 A | 7/1977 | Hetzel | 606/48 |
| 4,040,426 A | 8/1977 | Morrison, Jr. | 128/303 |
| 4,043,342 A | 8/1977 | Morrison, Jr. | 128/303 |
| 4,074,718 A | 2/1978 | Morrison, Jr. | 128/303 |
| 4,092,986 A | 6/1978 | Schneiderman | 128/303 |
| 4,116,198 A | 9/1978 | Roos | 128/303 |
| 4,181,131 A | 1/1980 | Ogiu | 128/303 |
| 4,184,492 A | 1/1980 | Meinke et al. | 128/303 |
| 4,202,337 A | 5/1980 | Hren et al. | 128/303 |
| 4,228,800 A | 10/1980 | Degler, Jr. et al. | 128/303 |
| 4,232,676 A | 11/1980 | Herczog | 128/303 |
| 4,248,231 A | 2/1981 | Herczog et al. | 128/303 |
| 4,301,802 A | 11/1981 | Poler | 606/48 |
| 4,326,529 A | 4/1982 | Doss et al. | 128/303 |
| 4,381,007 A | 4/1983 | Doss | 128/303 |
| 4,474,179 A | 10/1984 | Koch | 606/40 |
| 4,476,862 A | 10/1984 | Pao | 128/303 |
| 4,532,924 A | 8/1985 | Auth et al. | 128/303 |
| 4,548,207 A | 10/1985 | Reimels | 128/303 |
| 4,567,890 A | 2/1986 | Ohta et al. | 128/303 |
| 4,582,057 A | 4/1986 | Auth et al. | 606/31 |
| 4,590,934 A | 5/1986 | Malis et al. | 128/303 |
| 4,593,691 A | 6/1986 | Lindstrom et al. | 128/303 |
| 4,658,817 A | 4/1987 | Hardy | 606/14 |
| 4,660,571 A | 4/1987 | Hess et al. | 128/784 |
| 4,674,499 A | 6/1987 | Pao | 128/303 |
| 4,682,596 A | 7/1987 | Bales et al. | 128/303 |
| 4,706,667 A | 11/1987 | Roos | 128/303 |
| 4,709,698 A | 12/1987 | Johnston et al. | 606/41 |
| 4,727,874 A | 3/1988 | Bowers et al. | 128/303 |
| 4,765,331 A | 8/1988 | Petruzzi et al. | 128/303 |
| 4,785,823 A | 11/1988 | Eggers et al. | 128/692 |
| 4,805,616 A | 2/1989 | Pao | 128/303 |
| 4,823,791 A | 4/1989 | D'Amelio et al. | 123/303 |
| 4,832,048 A | 5/1989 | Cohen | 128/786 |
| 4,860,752 A | 8/1989 | Turner | 607/102 |
| 4,907,589 A | 3/1990 | Cosman | 606/34 |
| 4,920,978 A | 5/1990 | Colvin | 128/784 |
| 4,931,047 A | 6/1990 | Broadwin et al. | 604/22 |
| 4,936,281 A | 6/1990 | Stasz | 128/660 |
| 4,936,301 A | 6/1990 | Rexroth et al. | 606/45 |
| 4,943,290 A | 7/1990 | Rexroth et al. | 606/45 |
| 4,966,597 A | 10/1990 | Cosman | 606/50 |
| 4,967,765 A | 11/1990 | Turner et al. | 128/785 |
| 4,976,711 A | 12/1990 | Parins et al. | 606/48 |
| 4,979,948 A | 12/1990 | Geddes et al. | 606/33 |
| 4,998,933 A | 3/1991 | Eggers et al. | 606/41 |
| 5,007,908 A | 4/1991 | Rydell | 606/47 |
| 5,009,656 A | 4/1991 | Reimels | 606/48 |
| 5,035,696 A | 7/1991 | Rydell | 606/47 |
| 5,047,026 A | 9/1991 | Rydell | 606/48 |
| 5,047,027 A | 9/1991 | Rydell | 606/48 |
| 5,057,105 A | 10/1991 | Malone et al. | 606/28 |
| 5,057,106 A | 10/1991 | Kasevich et al. | 606/33 |
| 5,078,716 A | 1/1992 | Doll | 606/47 |
| 5,078,717 A | 1/1992 | Parins et al. | 606/48 |
| 5,080,660 A | 1/1992 | Buelna | 606/45 |
| 5,083,565 A | 1/1992 | Parins | 600/374 |
| 5,084,044 A | 1/1992 | Quint | 606/27 |
| 5,085,659 A | 2/1992 | Rydell | 606/47 |
| 5,088,997 A | 2/1992 | Delahuerga et al. | 606/42 |
| 5,098,431 A | 3/1992 | Rydell | 606/48 |
| 5,099,840 A | 3/1992 | Goble | 128/422 |
| 5,102,410 A | 4/1992 | Dressel | 606/15 |
| 5,108,391 A | 4/1992 | Flachenecker et al. | 606/38 |
| RE33,925 E | 5/1992 | Bales et al. | 606/48 |
| 5,112,330 A | 5/1992 | Nishigaki et al. | 606/46 |
| 5,122,138 A | 6/1992 | Manwaring | 606/46 |
| 5,125,928 A | 6/1992 | Parins et al. | 606/48 |
| 5,156,151 A | 10/1992 | Imran | 600/375 |
| 5,167,659 A | 12/1992 | Ohtomo et al. | 606/40 |
| 5,167,660 A | 12/1992 | Altendorf | 606/40 |
| 5,171,311 A | 12/1992 | Rydell et al. | 606/48 |
| 5,178,620 A | 1/1993 | Eggers et al. | 606/41 |
| 5,190,517 A | 3/1993 | Zieve et al. | 604/22 |
| 5,192,280 A | 3/1993 | Parins | 606/48 |
| 5,195,959 A | 3/1993 | Smith | 604/34 |
| 5,195,968 A | 3/1993 | Lundquist et al. | 604/95.04 |
| 5,196,007 A | 3/1993 | Ellman | 606/32 |
| 5,197,466 A | 3/1993 | Marchosky et al. | 128/399 |
| 5,197,963 A | 3/1993 | Parins | 606/46 |
| 5,207,675 A | 5/1993 | Canady | 606/40 |
| 5,217,457 A | 6/1993 | Delahuerga et al. | 606/42 |
| 5,217,459 A | 6/1993 | Kamerling | 606/48 |
| 5,249,585 A | 10/1993 | Turner et al. | 607/99 |
| 5,261,410 A | 11/1993 | Alfano et al. | 600/475 |
| 5,267,994 A | 12/1993 | Gentelia et al. | 606/15 |
| 5,267,997 A | 12/1993 | Farin et al. | 606/38 |
| 5,273,524 A | 12/1993 | Fox et al. | 604/21 |
| 5,277,201 A | 1/1994 | Stern | 607/98 |
| 5,281,216 A | 1/1994 | Klicek | 606/42 |
| 5,281,218 A | 1/1994 | Imran | 606/41 |
| 5,290,282 A | 3/1994 | Casscells | 606/29 |
| 5,300,069 A | 4/1994 | Hunsberger et al. | 606/37 |
| 5,306,238 A | 4/1994 | Fleenor | 606/42 |
| 5,312,400 A | 5/1994 | Bales et al. | 606/41 |
| 5,314,406 A | 5/1994 | Arias et al. | 604/21 |
| 5,324,254 A | 6/1994 | Phillips | 604/21 |
| 5,330,470 A | 7/1994 | Hagen | 606/42 |
| 5,334,140 A | 8/1994 | Phillips | 604/35 |
| 5,334,183 A | 8/1994 | Wuchinich | 606/46 |
| 5,334,193 A | 8/1994 | Nardella | 606/41 |
| 5,336,220 A | 8/1994 | Ryan et al. | 604/22 |
| 5,336,443 A | 8/1994 | Odashima | 252/511 |
| 5,342,357 A | 8/1994 | Nardella | 606/40 |
| 5,363,861 A | 11/1994 | Edwards et al. | 600/585 |
| 5,366,443 A | 11/1994 | Eggers et al. | 604/114 |
| 5,370,675 A | 12/1994 | Edwards et al. | 607/101 |
| 5,374,261 A | 12/1994 | Yoon | 604/385.01 |
| 5,375,588 A | 12/1994 | Yoon | 128/4 |
| 5,380,277 A | 1/1995 | Phillips | 604/33 |
| 5,380,316 A | 1/1995 | Aita | 606/7 |
| 5,383,876 A | 1/1995 | Nardella | 606/49 |
| 5,383,917 A | 1/1995 | Desai et al. | 607/702 |
| 5,389,096 A | 2/1995 | Aita | 606/15 |
| 5,395,312 A | 3/1995 | Desai | 604/22 |
| 5,395,363 A | 3/1995 | Billings et al. | 606/41 |
| 5,395,368 A | 3/1995 | Ellman et al. | 606/45 |
| 5,400,267 A | 3/1995 | Denen et al. | 702/59 |
| 5,401,272 A | 3/1995 | Perkins | 606/15 |
| 5,403,311 A | 4/1995 | Abele et al. | 606/49 |
| 5,417,687 A | 5/1995 | Nardella et al. | 606/32 |
| 5,419,767 A | 5/1995 | Eggers et al. | 604/114 |
| 5,423,810 A | 6/1995 | Goble et al. | 606/40 |
| 5,423,811 A | 6/1995 | Imran et al. | 606/41 |
| 5,423,812 A | 6/1995 | Ellman et al. | 606/45 |
| 5,423,882 A | 6/1995 | Jackman et al. | 607/122 |
| 5,436,566 A | 7/1995 | Thompson et al. | 324/713 |
| 5,437,662 A | 8/1995 | Nardella | 606/40 |
| 5,438,302 A | 8/1995 | Goble | 331/167 |
| 5,441,499 A | 8/1995 | Fritzsch | 606/45 |
| 5,451,224 A | 9/1995 | Goble et al. | 606/48 |
| 5,454,809 A | 10/1995 | Janssen | 606/41 |
| 5,456,662 A | 10/1995 | Edwards et al. | 604/22 |
| 5,458,596 A | 10/1995 | Lax et al. | 606/31 |
| 5,487,757 A | 1/1996 | Truckai et al. | 604/264 |
| 5,490,850 A | 2/1996 | Ellman et al. | 606/45 |
| 5,496,312 A | 3/1996 | Klicek | 606/34 |
| 5,496,314 A | 3/1996 | Eggers | 606/41 |
| 5,496,317 A | 3/1996 | Goble et al. | 606/48 |
| 5,505,728 A | 4/1996 | Ellman et al. | 606/39 |
| 5,505,730 A | 4/1996 | Edwards | 606/41 |
| 5,514,130 A | 5/1996 | Baker | 606/41 |
| 5,554,152 A | 9/1996 | Aita | 606/7 |
| 5,556,397 A | 9/1996 | Long et al. | 606/48 |
| 5,562,503 A | 10/1996 | Ellman et al. | 439/638 |
| 5,562,703 A | 10/1996 | Desai | 606/210 |
| 5,569,242 A | 10/1996 | Lax et al. | 606/42 |
| 5,571,100 A | 11/1996 | Goble et al. | 606/41 |
| 5,571,101 A | 11/1996 | Ellman et al. | 606/45 |
| 5,584,872 A | 12/1996 | LaFontaine et al. | 607/117 |
| 5,609,151 A | 3/1997 | Mulier et al. | 128/642 |
| 5,624,439 A | 4/1997 | Edwards et al. | 606/45 |
| 5,630,812 A | 5/1997 | Ellman et al. | 606/41 |

(56) References Cited

U.S. PATENT DOCUMENTS

| | | | |
|---|---|---|---|
| 5,633,578 A | 5/1997 | Eggers et al. ............... 323/301 |
| 5,647,869 A | 7/1997 | Goble et al. ................. 606/37 |
| 5,658,278 A | 8/1997 | Imran et al. ................. 606/41 |
| 5,662,680 A | 9/1997 | Desai ........................ 606/210 |
| 5,674,191 A | 10/1997 | Edwards et al. ............ 604/22 |
| 5,676,693 A | 10/1997 | LaFontaine et al. ........ 607/116 |
| 5,681,282 A | 10/1997 | Eggers et al. ............... 604/114 |
| 5,683,366 A | 11/1997 | Eggers et al. ............... 604/114 |
| 5,683,386 A | 11/1997 | Ellman et al. .............. 606/41 |
| 5,683,387 A | 11/1997 | Garito et al. ............... 606/45 |
| 5,688,267 A | 11/1997 | Panescu et al. ............. 606/41 |
| 5,695,495 A | 12/1997 | Ellman et al. .............. 606/41 |
| 5,697,281 A | 12/1997 | Eggers et al. ............... 604/114 |
| 5,697,536 A | 12/1997 | Eggers et al. ............... 604/114 |
| 5,697,882 A | 12/1997 | Eggers et al. ............... 604/114 |
| 5,697,909 A | 12/1997 | Eggers et al. ............... 604/114 |
| 5,700,262 A | 12/1997 | Acosta et al. ............... 606/48 |
| 5,707,349 A | 1/1998 | Edwards ..................... 604/22 |
| 5,718,702 A | 2/1998 | Edwards ..................... 606/41 |
| 5,725,524 A | 3/1998 | Mulier et al. ............... 606/41 |
| 5,728,094 A | 3/1998 | Edwards ..................... 606/41 |
| 5,733,282 A | 3/1998 | Ellman et al. .............. 606/45 |
| 5,738,114 A | 4/1998 | Edwards ..................... 128/898 |
| 5,743,870 A | 4/1998 | Edwards ..................... 604/22 |
| 5,746,224 A | 5/1998 | Edwards ..................... 128/898 |
| 5,749,869 A | 5/1998 | Lindenmeier et al. ...... 606/34 |
| 5,766,153 A | 6/1998 | Eggers et al. ............... 604/114 |
| 5,775,338 A | 7/1998 | Hastings ..................... 128/898 |
| 5,776,128 A | 7/1998 | Eggers ........................ 606/48 |
| 5,782,828 A | 7/1998 | Chen et al. ................. 606/42 |
| 5,800,379 A | 9/1998 | Edwards ..................... 604/22 |
| 5,800,429 A | 9/1998 | Edwards ..................... 606/41 |
| 5,807,395 A | 9/1998 | Mulier et al. ............... 606/41 |
| 5,810,764 A | 9/1998 | Eggers et al. ............... 604/23 |
| 5,810,809 A | 9/1998 | Rydell ........................ 606/49 |
| 5,817,049 A | 10/1998 | Edwards ..................... 604/22 |
| 5,820,580 A | 10/1998 | Edwards et al. ............ 604/22 |
| 5,823,197 A | 10/1998 | Edwards ..................... 128/898 |
| 5,827,277 A | 10/1998 | Edwards ..................... 606/41 |
| 5,836,875 A | 11/1998 | Webster, Jr. ................. 600/374 |
| 5,843,019 A | 12/1998 | Eggers et al. ............... 604/22 |
| 5,843,021 A | 12/1998 | Edwards et al. ............ 604/22 |
| 5,843,077 A | 12/1998 | Edwards ..................... 606/41 |
| 5,860,951 A | 1/1999 | Eggers ........................ 604/510 |
| 5,860,974 A | 1/1999 | Abele ......................... 606/41 |
| 5,860,975 A | 1/1999 | Goble et al. ................ 606/45 |
| 5,871,469 A | 2/1999 | Eggers et al. ............... 604/114 |
| 5,873,855 A | 2/1999 | Eggers et al. ............... 604/114 |
| 5,879,349 A | 3/1999 | Edwards ..................... 606/45 |
| 5,885,277 A | 3/1999 | Korth ......................... 606/35 |
| 5,888,198 A | 3/1999 | Eggers et al. ............... 604/114 |
| 5,891,095 A | 4/1999 | Eggers et al. ............... 604/114 |
| 5,891,134 A | 4/1999 | Goble et al. ................ 606/27 |
| 5,897,553 A | 4/1999 | Mulier ........................ 606/41 |
| 5,902,272 A | 5/1999 | Eggers et al. ............... 604/114 |
| 5,916,214 A | 6/1999 | Cosio et al. ................. 606/41 |
| 5,919,190 A | 7/1999 | Vandusseldorp ............ 606/46 |
| 5,921,983 A | 7/1999 | Shannon, Jr. ................ 606/45 |
| 5,944,715 A | 8/1999 | Goble et al. ................ 606/41 |
| 5,954,716 A | 9/1999 | Sharkey et al. ............. 606/32 |
| 5,988,171 A | 11/1999 | Sohn et al. .................. 128/848 |
| 6,004,319 A | 12/1999 | Goble et al. ................ 606/48 |
| 6,006,755 A | 12/1999 | Edwards ..................... 128/898 |
| 6,009,877 A | 1/2000 | Edwards ..................... 128/898 |
| 6,013,076 A | 1/2000 | Goble et al. ................ 606/41 |
| 6,015,406 A | 1/2000 | Goble et al. ................ 606/41 |
| 6,024,733 A | 2/2000 | Eggers et al. ............... 604/500 |
| 6,026,816 A | 2/2000 | McMillan et al. .......... 128/898 |
| 6,027,501 A | 2/2000 | Goble et al. ................ 606/41 |
| 6,032,674 A | 3/2000 | Eggers et al. ............... 128/898 |
| 6,039,734 A | 3/2000 | Goble et al. ................ 606/41 |
| 6,044,846 A | 4/2000 | Edwards ..................... 128/898 |
| 6,047,700 A | 4/2000 | Eggers et al. ............... 128/898 |
| 6,053,172 A | 4/2000 | Hovda et al. ............... 128/898 |
| 6,056,746 A | 5/2000 | Goble et al. ................ 606/48 |
| 6,063,079 A | 5/2000 | Hovda et al. ............... 606/41 |
| 6,066,134 A | 5/2000 | Eggers et al. ............... 606/32 |
| 6,066,139 A | 5/2000 | Ryan et al. .................. 606/50 |
| 6,068,628 A | 5/2000 | Fanton et al. ............... 606/41 |
| 6,071,281 A | 6/2000 | Burnside et al. ............ 606/41 |
| 6,073,052 A | 6/2000 | Zelickson et al. .......... 607/100 |
| 6,074,386 A | 6/2000 | Goble et al. ................ 606/34 |
| 6,086,585 A | 7/2000 | Hovda et al. ............... 606/45 |
| 6,090,106 A | 7/2000 | Goble et al. ................ 606/41 |
| 6,093,186 A | 7/2000 | Goble et al. ................ 606/34 |
| 6,102,046 A | 8/2000 | Weinstein et al. .......... 128/898 |
| 6,105,581 A | 8/2000 | Eggers et al. ............... 128/898 |
| 6,109,268 A | 8/2000 | Thapliyal et al. ........... 128/898 |
| 6,117,109 A | 9/2000 | Eggers et al. ............... 604/114 |
| 6,126,682 A | 10/2000 | Sharkey et al. ............. 607/96 |
| 6,142,992 A | 11/2000 | Cheng et al. ............... 606/34 |
| 6,149,620 A | 11/2000 | Baker et al. ................. 604/22 |
| 6,159,194 A | 12/2000 | Eggers et al. ............... 604/500 |
| 6,159,208 A | 12/2000 | Hovda et al. ............... 606/41 |
| 6,168,593 B1 | 1/2001 | Sharkey et al. ............. 606/34 |
| 6,174,309 B1 | 1/2001 | Wrublewski et al. ....... 606/45 |
| 6,179,824 B1 | 1/2001 | Eggers et al. ............... 604/500 |
| 6,179,836 B1 | 1/2001 | Eggers et al. ............... 606/45 |
| 6,183,469 B1 | 2/2001 | Thapliyal et al. ........... 606/41 |
| 6,190,381 B1 | 2/2001 | Olsen et al. ................. 606/32 |
| 6,203,542 B1 | 3/2001 | Ellsberry et al. ............ 606/41 |
| 6,210,402 B1 | 4/2001 | Olsen et al. ................. 606/32 |
| 6,210,405 B1 | 4/2001 | Goble et al. ................ 606/41 |
| 6,224,592 B1 | 5/2001 | Eggers et al. ............... 606/32 |
| 6,228,078 B1 | 5/2001 | Eggers ........................ 606/32 |
| 6,228,081 B1 | 5/2001 | Goble ......................... 606/34 |
| 6,234,178 B1 | 5/2001 | Goble et al. ................ 606/32 |
| 6,235,020 B1 | 5/2001 | Cheng et al. ............... 606/34 |
| 6,237,604 B1 | 5/2001 | Burnside et al. ............ 128/897 |
| 6,238,391 B1 | 5/2001 | Olsen et al. ................. 606/41 |
| 6,254,600 B1 | 7/2001 | Willink et al. .............. 606/41 |
| 6,258,086 B1 | 7/2001 | Ashley et al. ............... 606/41 |
| 6,261,286 B1 | 7/2001 | Goble et al. ................ 606/34 |
| 6,261,311 B1 | 7/2001 | Sharkey et al. ............. 607/96 |
| 6,264,652 B1 | 7/2001 | Eggers et al. ............... 606/41 |
| 6,270,460 B1 | 8/2001 | McCartan et al. .......... 600/459 |
| 6,270,476 B1 | 8/2001 | Santoianni et al. ......... 604/95.04 |
| 6,277,112 B1 | 8/2001 | Underwood et al. ....... 606/32 |
| 6,280,441 B1 | 8/2001 | Ryan ........................... 606/45 |
| 6,283,961 B1 | 9/2001 | Underwood et al. ....... 606/41 |
| 6,293,942 B1 | 9/2001 | Goble et al. ................ 606/38 |
| 6,296,636 B1 | 10/2001 | Cheng et al. ............... 606/32 |
| 6,296,638 B1 | 10/2001 | Davison et al. ............. 606/41 |
| 6,306,134 B1 | 10/2001 | Goble et al. ................ 606/42 |
| 6,308,089 B1 | 10/2001 | von der Rur et al. ....... 600/338 |
| 6,309,387 B1 | 10/2001 | Eggers et al. ............... 606/41 |
| 6,312,408 B1 | 11/2001 | Eggers et al. ............... 604/114 |
| 6,322,549 B1 | 11/2001 | Eggers et al. ............... 604/500 |
| 6,355,032 B1 | 3/2002 | Hovda et al. ............... 606/32 |
| 6,363,937 B1 | 4/2002 | Hovda et al. ............... 128/898 |
| 6,364,877 B1 | 4/2002 | Goble et al. ................ 606/34 |
| 6,379,350 B1 | 4/2002 | Sharkey et al. ............. 606/41 |
| 6,379,351 B1 | 4/2002 | Thapliyal et al. ........... 606/41 |
| 6,387,093 B1 | 5/2002 | Ellman et al. .............. 606/39 |
| 6,391,025 B1 | 5/2002 | Weinstein et al. .......... 606/41 |
| 6,411,852 B1 | 6/2002 | Danek et al. ............... 607/42 |
| 6,413,254 B1 | 7/2002 | Hissong et al. ............. 606/27 |
| 6,416,491 B1 | 7/2002 | Edwards et al. ............ 606/41 |
| 6,416,507 B1 | 7/2002 | Eggers et al. ............... 606/32 |
| 6,416,508 B1 | 7/2002 | Eggers et al. ............... 606/32 |
| 6,416,509 B1 | 7/2002 | Goble et al. ................ 606/37 |
| 6,427,089 B1 | 7/2002 | Knowlton ................... 607/101 |
| 6,432,103 B1 | 8/2002 | Ellsberry et al. ............ 606/41 |
| 6,464,699 B1 | 10/2002 | Swanson .................... 606/41 |
| 6,468,274 B1 | 10/2002 | Alleyne et al. ............. 606/32 |
| 6,468,275 B1 | 10/2002 | Wampler et al. ........... 606/48 |
| 6,482,201 B1 | 11/2002 | Olsen et al. ................. 606/41 |
| 6,491,690 B1 | 12/2002 | Goble et al. ................ 606/41 |
| 6,517,498 B1 | 2/2003 | Burbank et al. ............ 600/564 |
| 6,530,922 B2 | 3/2003 | Cosman ...................... 606/34 |
| 6,530,924 B1 | 3/2003 | Ellman et al. .............. 606/45 |
| 6,551,032 B1 | 4/2003 | Nolan et al. ................ 407/13 |
| 6,572,613 B1 | 6/2003 | Ellman et al. .............. 606/45 |
| 6,578,579 B2 | 6/2003 | Burnside .................... 128/897 |

(56) References Cited

U.S. PATENT DOCUMENTS

| | | | |
|---|---|---|---|
| 6,589,235 B2 | 7/2003 | Wong et al. | 606/32 |
| 6,589,237 B2 | 7/2003 | Woloszko et al. | 606/41 |
| 6,602,248 B1 | 8/2003 | Sharps et al. | 606/32 |
| 6,620,156 B1 | 9/2003 | Garito et al. | 606/50 |
| 6,632,193 B1 | 10/2003 | Davison et al. | 604/22 |
| 6,632,220 B1 | 10/2003 | Eggers et al. | 606/41 |
| 6,702,810 B2 | 3/2004 | McClurken et al. | 606/34 |
| 6,736,810 B2 | 5/2004 | Hoey et al. | 606/34 |
| 6,746,447 B2 | 6/2004 | Davison et al. | 606/41 |
| 6,749,604 B1 | 6/2004 | Eggers et al. | 606/41 |
| 6,749,608 B2 | 6/2004 | Garito et al. | 606/45 |
| 6,770,071 B2 | 8/2004 | Woloszko et al. | 606/41 |
| 6,780,178 B2 | 8/2004 | Palanker et al. | 600/41 |
| 6,780,180 B1 | 8/2004 | Goble et al. | 606/41 |
| 6,802,842 B2 | 10/2004 | Ellman et al. | 606/45 |
| 6,837,887 B2 | 1/2005 | Woloszko et al. | 606/41 |
| 6,837,888 B2 | 1/2005 | Ciarrocca et al. | 606/41 |
| 6,896,674 B1 | 5/2005 | Woloszko et al. | 606/41 |
| 6,920,883 B2 | 7/2005 | Bessette et al. | 128/898 |
| 6,929,640 B1 | 8/2005 | Underwood et al. | 606/32 |
| 6,942,662 B2 | 9/2005 | Goble et al. | 606/48 |
| 6,949,096 B2 | 9/2005 | Davison et al. | 606/41 |
| 6,955,172 B2 | 10/2005 | Nelson et al. | 128/848 |
| 6,960,204 B2 | 11/2005 | Eggers et al. | 606/32 |
| 6,974,453 B2 | 12/2005 | Woloszko et al. | 606/41 |
| 6,984,231 B2 | 1/2006 | Goble et al. | 606/37 |
| 6,991,631 B2 | 1/2006 | Woloszko et al. | 606/41 |
| 7,004,941 B2 | 2/2006 | Tvinnereim et al. | 606/41 |
| 7,041,102 B2 | 5/2006 | Truckai et al. | 606/51 |
| 7,066,936 B2 | 6/2006 | Ryan | 606/45 |
| 7,070,596 B1 | 7/2006 | Woloszko et al. | 606/41 |
| 7,090,672 B2 | 8/2006 | Underwood et al. | 606/41 |
| 7,094,215 B2 | 8/2006 | Davison et al. | 604/22 |
| 7,104,986 B2 | 9/2006 | Hovda et al. | 606/32 |
| 7,131,969 B1 | 11/2006 | Hovda et al. | 606/45 |
| 7,160,296 B2 | 1/2007 | Pearson et al. | 606/42 |
| 7,169,143 B2 | 1/2007 | Eggers et al. | 606/32 |
| 7,179,255 B2 | 2/2007 | Lettice et al. | 606/32 |
| 7,186,234 B2 | 3/2007 | Dahla et al. | 604/22 |
| 7,192,428 B2 | 3/2007 | Eggers et al. | 606/41 |
| 7,195,630 B2 | 3/2007 | Ciarrocca | 606/42 |
| 7,201,750 B1 | 4/2007 | Eggers et al. | 606/41 |
| 7,217,268 B2 | 5/2007 | Eggers et al. | 606/32 |
| 7,241,293 B2 | 7/2007 | Davison | 600/410 |
| 7,270,658 B2 | 9/2007 | Woloszko et al. | 606/32 |
| 7,270,659 B2 | 9/2007 | Hovda et al. | 606/32 |
| 7,270,661 B2 | 9/2007 | Dahla et al. | 606/41 |
| 7,276,063 B2 | 10/2007 | Davison et al. | 606/45 |
| 7,297,143 B2 | 11/2007 | Woloszko et al. | 606/41 |
| 7,297,145 B2 | 11/2007 | Ormsby et al. | 606/41 |
| 7,318,823 B2 | 1/2008 | Sharps et al. | 606/32 |
| 7,331,956 B2 | 2/2008 | Hovda et al. | 606/32 |
| RE40,156 E | 3/2008 | Sharps et al. | 606/32 |
| 7,357,798 B2 | 4/2008 | Sharps et al. | 606/32 |
| 7,387,625 B2 | 6/2008 | Hovda et al. | 606/32 |
| 7,419,488 B2 | 9/2008 | Ciarrocca et al. | 606/41 |
| 7,429,260 B2 | 9/2008 | Underwood et al. | 606/32 |
| 7,429,262 B2 | 9/2008 | Woloszko et al. | 606/46 |
| 7,435,247 B2 | 10/2008 | Woloszko et al. | 604/41 |
| 7,442,191 B2 | 10/2008 | Hovda et al. | 606/41 |
| 7,445,618 B2 | 11/2008 | Eggers et al. | 604/48 |
| 7,449,021 B2 | 11/2008 | Underwood et al. | 606/32 |
| 7,462,178 B2 | 12/2008 | Woloszko et al. | 607/105 |
| 7,468,059 B2 | 12/2008 | Eggers et al. | 606/32 |
| 7,491,200 B2 | 2/2009 | Underwood et al. | 606/32 |
| 7,507,236 B2 | 3/2009 | Eggers et al. | 606/41 |
| 7,572,251 B1 | 8/2009 | Davison et al. | 604/500 |
| 7,632,267 B2 | 12/2009 | Dahla | 606/41 |
| 7,691,101 B2 | 4/2010 | Davison et al. | 606/41 |
| 7,704,249 B2 | 4/2010 | Woloszko et al. | 606/48 |
| 7,708,733 B2 | 5/2010 | Sanders et al. | 606/41 |
| 7,824,398 B2 | 11/2010 | Woloszko et al. | 606/45 |
| 7,879,034 B2 | 2/2011 | Woloszko et al. | 606/48 |
| 7,892,230 B2 | 2/2011 | Woloszko et al. | 606/41 |
| 7,901,403 B2 | 3/2011 | Woloszko et al. | 606/48 |
| 8,568,405 B2 * | 10/2013 | Cox et al. | 606/41 |
| 8,747,401 B2 | 6/2014 | Gonzalez et al. | 606/41 |
| 9,011,428 B2 | 4/2015 | Nguyen et al. | |
| 2002/0026186 A1 | 2/2002 | Woloszko et al. | 606/41 |
| 2002/0029036 A1 | 3/2002 | Goble et al. | 606/38 |
| 2002/0049438 A1 | 4/2002 | Sharkey et al. | 606/41 |
| 2003/0013986 A1 | 1/2003 | Saadat | 600/549 |
| 2003/0014050 A1 | 1/2003 | Sharkey et al. | 606/45 |
| 2003/0088245 A1 | 5/2003 | Woloszko et al. | 606/41 |
| 2003/0097129 A1 | 5/2003 | Davison et al. | 606/41 |
| 2003/0158545 A1 | 8/2003 | Hovda et al. | 606/32 |
| 2003/0171743 A1 | 9/2003 | Tasto et al. | 606/32 |
| 2003/0208196 A1 | 11/2003 | Stone | 606/41 |
| 2003/0212396 A1 | 11/2003 | Eggers et al. | 606/41 |
| 2004/0054366 A1 * | 3/2004 | Davison et al. | 606/39 |
| 2004/0116922 A1 | 6/2004 | Hovda et al. | 606/41 |
| 2004/0127893 A1 | 7/2004 | Hovda | 606/41 |
| 2004/0230190 A1 | 11/2004 | Dahla et al. | 604/41 |
| 2005/0004634 A1 | 1/2005 | Hovda et al. | 606/41 |
| 2005/0043728 A1 | 2/2005 | Ciarrocca | 606/48 |
| 2005/0261754 A1 | 11/2005 | Woloszko et al. | 606/32 |
| 2005/0283149 A1 | 12/2005 | Thorne et al. | 606/48 |
| 2005/0288665 A1 | 12/2005 | Woloszko et al. | 606/41 |
| 2006/0036237 A1 | 2/2006 | Davison et al. | 606/41 |
| 2006/0095031 A1 | 5/2006 | Ormsby | 606/34 |
| 2006/0129145 A1 | 6/2006 | Woloszko et al. | 606/41 |
| 2006/0178670 A1 | 8/2006 | Woloszko et al. | 606/48 |
| 2006/0189971 A1 | 8/2006 | Eggers et al. | 606/32 |
| 2006/0253117 A1 | 11/2006 | Hovda et al. | 128/898 |
| 2006/0259025 A1 | 11/2006 | Dahla | 607/108 |
| 2006/0259031 A1 * | 11/2006 | Carmel et al. | 606/41 |
| 2007/0010808 A1 | 1/2007 | Dahla | 606/41 |
| 2007/0106288 A1 | 5/2007 | Woloszko et al. | 606/41 |
| 2007/0149966 A1 | 6/2007 | Dahla et al. | 606/41 |
| 2007/0161981 A1 | 7/2007 | Sanders et al. | 606/41 |
| 2007/0208335 A1 | 9/2007 | Woloszko et al. | 606/41 |
| 2007/0282323 A1 | 12/2007 | Woloszko et al. | 606/41 |
| 2008/0200972 A1 | 8/2008 | Rittman et al. | 607/117 |
| 2010/0204690 A1 | 8/2010 | Bigley et al. | 606/41 |
| 2012/0101494 A1 | 4/2012 | Cadouri et al. | 606/41 |
| 2012/0191089 A1 | 7/2012 | Gonzalez et al. | 606/45 |
| 2012/0226273 A1 | 9/2012 | Nguyen et al. | 606/41 |
| 2013/0066317 A1 | 3/2013 | Evans et al. | 606/48 |
| 2013/0197506 A1 | 8/2013 | Evans et al. | 606/48 |
| 2014/0200581 A1 | 7/2014 | Aluru et al. | 606/48 |

FOREIGN PATENT DOCUMENTS

| | | | |
|---|---|---|---|
| DE | 102014003645.00 | 9/2014 | A61B 18/12 |
| EP | 0509670 | 10/1992 | A61B 17/39 |
| EP | 0703461 A2 | 3/1996 | G01B 27/02 |
| EP | 0740926 A2 | 11/1996 | A61B 17/39 |
| EP | 0754437 A2 | 1/1997 | A61B 17/39 |
| EP | 0694290 B1 | 11/2000 | A61B 18/04 |
| EP | 2198799 | 6/2010 | A61B 18/14 |
| FR | 2313949 | 1/1977 | A61N 3/02 |
| GB | 2 308 979 | 7/1997 | A61B 17/36 |
| GB | 2 308 980 | 7/1997 | A61B 17/36 |
| GB | 2 308 981 | 7/1997 | A61B 17/36 |
| GB | 2 327 350 | 1/1999 | A61B 17/39 |
| GB | 2 327 351 | 1/1999 | A61B 17/39 |
| GB | 2 327 352 | 1/1999 | A61B 17/39 |
| GB | 2479582 | 10/2011 | A61B 18/14 |
| JP | 57-57802 | 4/1982 | A61B 1/00 |
| JP | 57-117843 | 7/1982 | A61B 17/39 |
| JP | 58-13213 | 1/1983 | A61B 18/12 |
| JP | 10-43198 | 2/1998 | A61B 17/42 |
| WO | 90/03152 | 4/1990 | A61B 17/39 |
| WO | 90/07303 | 7/1990 | A61B 17/39 |
| WO | 92/21278 | 12/1992 | A61B 5/04 |
| WO | 93/13816 | 7/1993 | A61B 17/36 |
| WO | 93/20747 | 10/1993 | A61B 5/00 |
| WO | 94/04220 | 3/1994 | |
| WO | 94/08654 | 4/1994 | A61M 37/00 |
| WO | 94/10924 | 5/1994 | A61B 17/39 |
| WO | 94/26228 | 11/1994 | A61G 17/36 |
| WO | 95/34259 | 12/1995 | A61F 5/48 |
| WO | 96/00042 | 1/1996 | A61B 17/39 |
| WO | 96/23449 | 8/1996 | A61B 17/39 |

(56) References Cited

FOREIGN PATENT DOCUMENTS

| WO | 96/37156 | 11/1996 | ............ A61B 17/00 |
|---|---|---|---|
| WO | 96/39914 | 12/1996 | ............ A61B 1/00 |
| WO | 97/00646 | 1/1997 | ............ A61B 17/39 |
| WO | 97/00647 | 1/1997 | ............ A61B 17/39 |
| WO | 97/15237 | 5/1997 | ............ A61B 18/12 |
| WO | 97/18765 | 5/1997 | ............ A61B 17/36 |
| WO | 97/24073 | 7/1997 | ............ A61B 17/39 |
| WO | 97/24074 | 7/1997 | ............ A61B 17/39 |
| WO | 97/24993 | 7/1997 | ............ A61B 17/39 |
| WO | 97/24994 | 7/1997 | ............ A61B 17/39 |
| WO | 97/30644 | 8/1997 | ............ A61B 17/39 |
| WO | 97/30645 | 8/1997 | ............ A61B 17/39 |
| WO | 97/30646 | 8/1997 | ............ A61B 17/39 |
| WO | 97/30647 | 8/1997 | ............ A61B 17/39 |
| WO | 97/41785 | 11/1997 | ............ A61B 17/39 |
| WO | 97/41786 | 11/1997 | ............ A61B 17/39 |
| WO | 97/41787 | 11/1997 | ............ A61B 17/39 |
| WO | 97/41788 | 11/1997 | ............ A61B 17/39 |
| WO | 97/43969 | 11/1997 | ............ A61B 17/39 |
| WO | 97/43970 | 11/1997 | ............ A61B 17/39 |
| WO | 97/43972 | 11/1997 | ............ A61B 17/39 |
| WO | 97/43973 | 11/1997 | ............ A61B 17/39 |
| WO | 97/44092 | 11/1997 | ............ A61B 17/39 |
| WO | 97/48345 | 12/1997 | ............ A61B 17/39 |
| WO | 97/48346 | 12/1997 | ............ A61B 17/39 |
| WO | 98/03117 | 1/1998 | ............ A61B 17/00 |
| WO | 98/07468 | 2/1998 | ............ A61N 1/40 |
| WO | 98/27879 | 7/1998 | ............ A61B 17/36 |
| WO | 98/27880 | 7/1998 | ............ A61B 17/39 |
| WO | 99/08613 | 2/1999 | ............ A61B 17/36 |
| WO | 99/09919 | 3/1999 | ............ A61B 18/12 |
| WO | 99/17690 | 4/1999 | ............ A61F 7/12 |
| WO | 99/30655 | 6/1999 | ............ A61F 7/12 |
| WO | 99/51155 | 10/1999 | ............ A61B 17/36 |
| WO | 99/51158 | 10/1999 | ............ A61B 17/39 |
| WO | 00/62698 | 10/2000 | ............ A61B 18/14 |
| WO | 01/87154 | 5/2001 | ............ A61B 5/05 |
| WO | 02/36028 | 5/2002 | ............ A61B 18/12 |
| WO | 02/085230 | 10/2002 | ............ A61B 18/14 |
| WO | 03/005882 | 1/2003 | ............ A61B 18/14 |
| WO | 03/024305 | 3/2003 | |
| WO | 03/047446 | 6/2003 | ............ A61B 18/12 |
| WO | 03/068095 | 8/2003 | ............ A61B 18/14 |
| WO | 2004/050171 | 6/2004 | |
| WO | 2005/125287 | 12/2005 | ............ A61B 18/00 |
| WO | 2006/002337 | 1/2006 | ............ A61B 18/14 |
| WO | 2006/125007 | 11/2006 | ............ A61B 18/14 |

OTHER PUBLICATIONS

BiLAP Generator Settings, Jun. 1991.
BiLAP IFU 910026-001 Rev A for BiLAP Model 3525, J-Hook, 4 pgs, May 20, 1991.
BiLAP IFU 910033-002 Rev A for BiLAP Model 3527, L-Hook; BiLAP Model 3525, J-Hook; BiLAP Model 3529, High Angle, 2 pgs, Nov. 30, 1993.
Codman & Shurtleff, Inc. "The Malis Bipolar Coagulating and Bipolar Cutting System CMC-II" brochure, early, 2 pgs, 1991.
Codman & Shurtleff, Inc. "The Malis Bipolar Electrosurgical System CMC-III Instruction Manual" , 15 pgs, Jul. 1991.
Cook et al., "Therapeutic Medical Devices: Application and Design" , Prentice Hall, Inc., 3pgs, 1982.
Dennis et al. "Evolution of Electrofulguration in Control of Bleeding of Experimental Gastric Ulcers," Digestive Diseases and Sciences, vol. 24, No. 11, 845-848, Nov. 1979.
Dobbie, A.K., "The Electrical Aspects of Surgical Diathermy, Bio Medical Engineering" *Bio-Medical Engineering* vol. 4, pp. 206-216, May 1969.
Elsasser, V.E. et al., "An Instrument for Transurethral Resection without Leakage of Current" *Acta Medicotechnica* vol. 24, No. 4, pp. 129-134, 1976.
Geddes, "Medical Device Accidents: With Illustrative Cases" CRC Press, 3 pgs, 1998.

Honig, W., "The Mechanism of Cutting in Electrosurgery" *IEEE* pp. 58-65, 1975.
Kramolowsky et al. "The Urological App of Electorsurgery" *J. of Urology* vol. 146, pp. 669-674, 1991.
Kramolowsky et al. "Use of 5F Bipolar Electrosurgical Probe in Endoscopic Urological Procedures" *J. of Urology* vol. 143, pp. 275-277, 1990.
Lee, B et al. "Thermal Compression and Molding of Artherosclerotic Vascular Tissue with Use" JACC vol. 13(5), pp. 1167-1171, 1989.
Letter from Department of Health to Jerry Malis dated Jan. 24, 1991, 3 pgs.
Letter from Department of Health to Jerry Malis dated Jul. 25, 1985, 1 pg.
Letter from Jerry Malis to FDA dated Jul. 25, 1985, 2 pgs.
Lu, et al., "Electrical Thermal Angioplasty: Catheter Design Features, in Vitro Tissue Ablation Studies and in Vitro Experimental Findings," *Am J. Cardiol* vol. 60, pp. 1117-1122, Nov. 1, 1987.
Malis, L., "Electrosurgery, Technical Note," *J. Neursurg.*, vol. 85, pp. 970-975, Nov. 1996.
Malis, L., "Excerpted from a seminar by Leonard I. Malis, M.D. at the 1995 American Association of Neurological Surgeons Meeting," 1pg, 1995.
Malis, L., "Instrumentation for Microvascular Neurosurgery" *Cerebrovascular Surgery*, vol. 1, pp. 245- 260, 1985.
Malis, L., "New Trends in Microsurgery and Applied Technology," *Advanced Technology in Neurosurgery*, pp. 1-16, 1988.
Malis, L., "The Value of Irrigation During Bipolar Coagulation" See ARTC 21602, 1 pg, Apr. 9, 1993.
Nardella, P.C., *SPIE* 1068: pp. 42-49, Radio Frequency Energy and Impedance Feedback, 1989.
O'Malley, Schaum's Outline of Theory and Problems of Basic Circuit Analysis, McGraw-Hill, $2^{nd}$ Ed., pp. 3-5, 1992.
Olsen MD, Bipolar Laparoscopic Cholecstectomy Lecture (marked confidential), 12 pgs, Oct. 7, 1991.
Pearce, John A. "Electrosurgery", pp. 17, 69-75, 87, John Wiley & Sons, New York, 1986.
Pearce, John A., "Electrosurgery", Handbook of Biomedical Engineering, chapter 3, Academic Press Inc., N.Y., pp. 98-113, 1988.
Piercey et al., "Electrosurgical Treatment of Experimental Bleeding Canine Gastric Ulcers" *Gastroenterology* vol. 74(3), pp. 527-534, 1978.
Protell et al., "Computer-Assisted Electrocoagulation: Bipolar v. Monopolar in the Treatment of Experimental Canine Gastric Ulcer Bleeding," *Gastroenterology* vol. 80, No. 3, pp. 451-455, 1981.
Ramsey et al., "A Comparison of Bipolar and Monopolar Diathermy Probes in Experimental Animals", *Urological Research* vol. 13, pp. 99-102, 1985.
Selikowitz et al., "Electric Current and Voltage Recordings on the Myocardium During Electrosurgical Procedures in Canines," *Surgery, Gynecology & Obstetrics*, vol. 164, pp. 219-224, Mar. 1987.
Shuman, "Bipolar Versus Monopolar Electrosurgery: Clinical Applications," *Dentistry Today*, vol. 20, No. 12, 7 pgs, Dec. 2001.
Slager et al. "Spark Erosion of Arteriosclerotic Plaques" *Z. Kardiol.* 76:Suppl. 6, pp. 67-71, 1987.
Slager et al. "Vaporization of Atheroscleroticce Plaques by Spark Erosion" *JACC* 5(6): pp. 1382-1386, Jun. 1985.
Stoffels, E. et al., "Investigation on the Interaction Plasma-Bone Tissue", E-MRS Spring Meeting, 1 pg, Jun. 18-21, 2002.
Stoffels, E. et al., "Biomedical Applications of Plasmas", Tutorial presented prior to the $55^{th}$ Gaseous Electronics Conference in Minneapolis, MN, 41 pgs, Oct. 14, 2002.
Stoffels, E. et al., "Plasma Interactions with Living Cells", Eindhoven University of Technology, 1 pg, 2002.
Stoffels, E. et al., "Superficial Treatment of Mammalian Cells using Plasma Needle", J. Phys. D: Appl. Phys. 26, pp. 2908-2913, Nov. 19, 2003.
Stoffels, E. et al., "Plasma Needle", Eindhoven University of Technology, 1 pg, Nov. 28, 2003.
Stoffels, E. et al., "Plasma Physicists Move into Medicine", Physicsweb, 1 pg, Nov. 2003.
Stoffels, E. et al., "Plasma Treated Tissue Engineered Skin to Study Skin Damage", Biomechanics and Tissue Engineering, Materials Technology, 1 pg, 2003.

(56) References Cited

OTHER PUBLICATIONS

Stoffels, E. et al., "Plasma Treatment of Dental Cavities: A Feasibility Study", IEEE Transaction on Plasma Science, vol. 32, No. 4, pp. 1540-1542, Aug. 2004.
Stoffels, E. et al., "The Effects of UV Irradiation and Gas Plasma Treatment on Living Mammalian Cells and Bacteria: A Comparative Approach", IEEE Transaction on Plasma Science, vol. 32, No. 4, pp. 1544-1550, Aug. 2004.
Stoffels, E. et al., "Electrical and Optical Characterization of the Plasma Needle", New Journal of Physics 6, pp. 1-14, Oct. 28, 2004.
Stoffels, E. et al., "Where Plasma Meets Plasma", Eindhoven University of Technology, 23 pgs, 2004.
Stoffels, E. et al., "Gas Plasma effects on Living Cells", Physica Scripta, T107, pp. 79-82, 2004.
Stoffels, E. et al., "Plasma Treatment of Mammalian Vascular Cells: A Quantitative Description", IEEE Transaction on Plasma Science, vol. 33, No. 2, pp. 771-775, Apr. 2005.
Stoffels, E. et al., "Deactivation of *Escherichia coli* by the Plasma Needle", J. Phys. D: Appl. Phys. 38, pp. 1716-1721, May 20, 2005.
Stoffels, E. et al., "Development of a Gas Plasma Catheter for Gas Plasma Surgery", XXVIIth ICPIG, Endoven University of Technology, pp. 18-22, Jul. 2005.
Stoffels, E. et al., "Development of a Smart Positioning Sensor for the Plasma Needle", Plasma Sources Sci. Technol. 15, pp. 582-589, Jun. 27, 2006.
Stoffels, E. et al., Killing of *S. mutans* Bacteria Using a Plasma Needle at Atmospheric Pressure, IEEE Transaction on Plasma Science, vol. 34, No. 4, pp. 1317-1324, Aug. 2006.
Stoffels, E. et al., "Plasma-Needle Treatment of Substrates with Respect to Wettability and Growth of *Excherichia coli* and *Streptococcus mutans*", IEEE Transaction on Plasma Science, vol. 34, No. 4, pp. 1325-1330, Aug. 2006.
Stoffels, E. et al., "Reattachment and Apoptosis after Plasma-Needle Treatment of Cultured Cells", IEEE Transaction on Plasma Science, vol. 34, No. 4, pp. 1331-1336, Aug. 2006.
Stoffels, E. et al., "UV Excimer Lamp Irradiation of Fibroblasts: The Influence on Antioxidant Homostasis", IEEE Transaction on Plasma Science, vol. 34, No. 4, pp. 1359-1364, Aug. 2006.
Stoffels, E. et al., "Plasma Needle for in Vivo Medical Treatment: Recent Developments and Perspectives", Plasma Sources Sci. Technol. 15, pp. S169-S180, Oct. 6, 2006.
Swain, C.P., et al., "Which Electrode, A Comparison of four endoscopic methods of electrocoagulation in experimental bleeding ulcers" *Gut* vol. 25, pp. 1424-1431, 1987.
Tucker, R. et al., Abstract P14-11, p. 248, "A Bipolar Electrosurgical Turp Loop", Nov. 1989.
Tucker, R. et al. "A Comparison of Urologic Application of Bipolar Versus Monopolar Five French Electrosurgical Probes" *J. of Urology* vol. 141, pp. 662-665, 1989.
Tucker, R. et al. "In vivo effect of 5 French Bipolar and Monopolar Electrosurgical Probes on the Porcine Bladder" *Urological Research* vol. 18, pp. 291-294, 1990.
Tucker, R. et al., "Demodulated Low Frequency Currents from Electrosurgical Procedures," *Surgery, Gynecology and Obstetrics*, 159:39-43, 1984.
Tucker et al. "The interaction between electrosurgical generators, endoscopic electrodes, and tissue," Gastrointestinal Endoscopy, vol. 38, No. 2, pp. 118-122, 1992.
Valley Forge Scientific Corp., "Summary of Safety and Effective Information from 510K", 2pgs, 1991.
Valley Forge's New Products, CLINICA, 475, 5, Nov. 6, 1991.
Valleylab SSE2L Instruction Manual, 11 pgs, Jan. 6, 1983.
Valleylab, Inc. "Valleylab Part No. 945 100 102 A" Surgistat Service Manual, pp. 1-46, Jul. 1988.
Wattiez, Arnaud et al., "Electrosurgery in Operative Endoscopy," Electrosurgical Effects, Blackwell Science, pp. 85-93, 1995.
Wyeth, "Electrosurgical Unit" pp. 1181-1202, 2000.
Rand et al., "Effect of Elecctrocautery on Fresh Human Articular Cartilage", J. Arthro. Surg., vol. 1, pp. 242-246, 1985.
European Search Report for EP00123324.6 4 pgs, Mailed Jan. 16, 2001.
European Search Report for EP00928246 4 pgs, Mailed Mar. 7, 2008.
European Search Report for EP09153983 9 pgs, Mailed Apr. 1, 2009.
European Search Report for EP98964730.0 3 pgs, Mailed Nov. 20, 2000.
European Search Report for EP99922855.4 3 pgs, Aug. 2, 2001.
European Search Report for EP05762588 3 pgs, Apr. 12, 2010.
European Search Report for EP06760025.4 5 pgs, Nov. 10, 2010.
PCT International Preliminary Examination Report for PCT/US00/10674 4pgs, Mailed Mar. 7, 2001.
PCT International Preliminary Examination Report for PCT/US98/26624 4pgs, Mailed Oct. 12, 1999.
PCT International Preliminary Examination Report for PCT/US99/10062 3pgs, Jun. 20, 2000.
PCT International Preliminary Report on Patentability for PCT/US05/22373 4pgs, Dec. 28, 2006.
PCT International Preliminary Report on Patentability for PCT/US06/19095 6pgs, Nov. 20, 2007.
PCT International Search Report for PCT/US00/10674 1 pg, Mailed Jul. 27, 2000.
PCT International Search Report for PCT/US03/38782 1pg, Mailed Jun. 30, 2004.
PCT International Search Report for PCT/US05/22373 1 pg, Mailed Oct. 3, 2006.
PCT International Search Report for PCT/US06/19095 2 pgs, Mailed Oct. 4, 2007.
PCT International Search Report for PCT/US96/08077 1 page, Mailed Sep. 16, 1996.
PCT International Search Report for PCT/US98/26624 1 page, Mailed Mar. 3, 1999.
PCT International Search Report for PCT/US99/10062 1 pg, Mailed Aug. 23, 1999.
UK Search Report for GB1111622.5 4pgs, Oct. 26, 2011.
UK Search Report for GB1202275.2 7pgs, May 11, 2012.
UK Search Report for GB1202275.2 5pgs, Sep. 12, 2014.
UK Combined Search and Exam Report for GB1404394.7 6pgs, Sep. 17, 2014.

\* cited by examiner

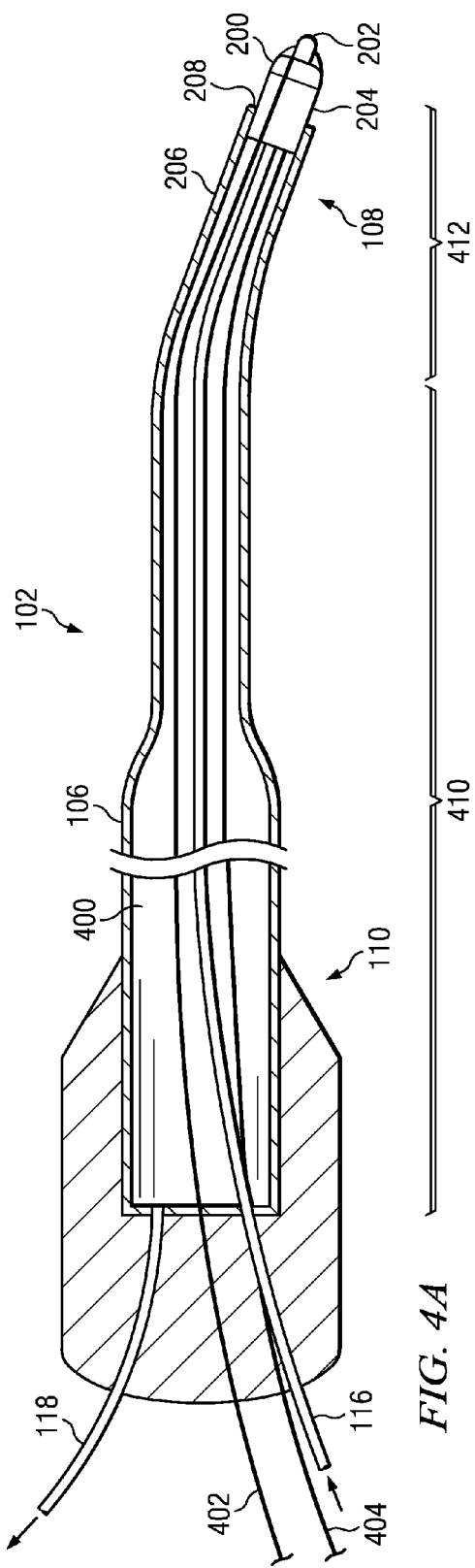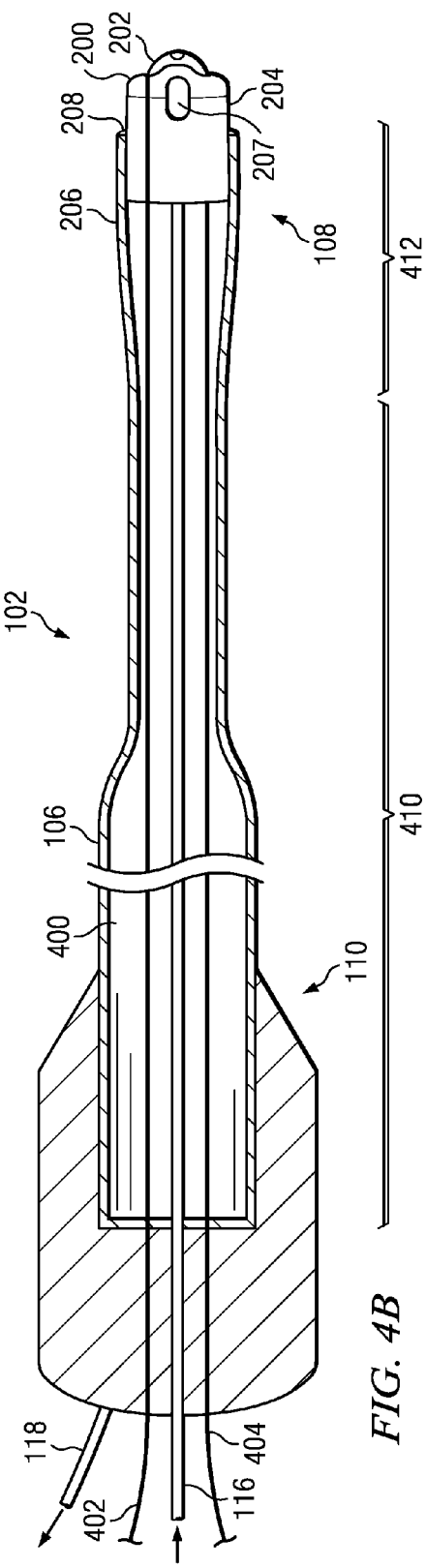

_US 9,168,082 B2_

FINE DISSECTION ELECTROSURGICAL DEVICE

BACKGROUND

The field of electrosurgery includes a number of loosely related surgical techniques which have in common the application of electrical energy to modify the structure or integrity of patient tissue. Electrosurgical procedures usually operate through the application of very high frequency currents to cut or ablate tissue structures, where the operation can be monopolar or bipolar. Monopolar techniques rely on a separate electrode for the return of current that is placed away from the surgical site on the body of the patient, and where the surgical device defines only a single electrode pole that provides the surgical effect. Bipolar devices comprise two or more electrodes on the same support for the application of current between their surfaces.

Electrosurgical procedures and techniques are particularly advantageous since they generally reduce patient bleeding and trauma associated with cutting operations. Additionally, electrosurgical ablation procedures, where tissue surfaces and volume may be reshaped, cannot be duplicated through other treatment modalities.

Radiofrequency (RF) energy is used in a wide range of surgical procedures because it provides efficient tissue resection and coagulation and relatively easy access to the target tissues through a portal or cannula. Conventional monopolar high frequency electrosurgical devices typically operate by creating a voltage difference between the active electrode and the target tissue, causing an electrical arc to form across the physical gap between the electrode and tissue. At the point of contact of the electric arcs with tissue, rapid tissue heating occurs due to high current density between the electrode and tissue. This high current density causes cellular fluids to rapidly vaporize into steam, thereby producing a "cutting effect" along the pathway of localized tissue heating. Thus, the tissue is parted along the pathway of evaporated cellular fluid, inducing undesirable collateral tissue damage in regions surrounding the target tissue site. This collateral tissue damage often causes indiscriminate destruction of tissue, resulting in the loss of the proper function of the tissue. In addition, the device does not remove any tissue directly, but rather depends on destroying a zone of tissue and allowing the body to eventually remove the destroyed tissue.

Present electrosurgical techniques used for tissue ablation may suffer from an inability to provide the ability for fine dissection of soft tissue. The distal end of electrosurgical devices is wide and flat, creating a relatively wide area of volumetric tissue removal and making fine dissections along tissue planes more difficult to achieve because of the lack of precision provided by the current tip geometries. In addition, identification of the plane is more difficult because the large ablated area and overall size of the device tip obscures the physician's view of the surgical field. The inability to provide for fine dissection of soft tissue is a significant disadvantage in using electrosurgical techniques for tissue ablation, particularly in arthroscopic, otolaryngological, and spinal procedures.

Traditional monopolar RF systems can provide fine dissection capabilities of soft tissue, but may also cause a high level of collateral thermal damage. Further, these devices may suffer from an inability to control the depth of necrosis in the tissue being treated. The high heat intensity generated by these systems causes burning and charring of the surrounding tissue, leading to increased pain and slower recovery of the remaining tissue. Further, the desire for an electrosurgical device to provide for fine dissection of soft tissue may compromise the ability to provide consistent ablative cutting without significant collateral damage while allowing for concomitant hemostasis and good coagulation of the remaining tissue.

Accordingly, improved systems and methods are still desired for performing fine dissection of soft tissue via electrosurgical ablation of tissue. In particular, improved systems operable to provide a combination of smooth and precise cutting, effective concomitant hemostasis during cutting, and efficient coagulation ability in fine dissection soft tissue procedures would provide a competitive advantage.

BRIEF DESCRIPTION OF THE DRAWINGS

For a detailed description of exemplary embodiments, reference will now be made to the accompanying drawings in which:

FIG. 4A shows a cross-sectional view of a wand in accordance with at least some embodiments;

FIG. 4B shows a cross-sectional view of a wand in accordance with at least some embodiments;

NOTATION AND NOMENCLATURE

Figure 1:
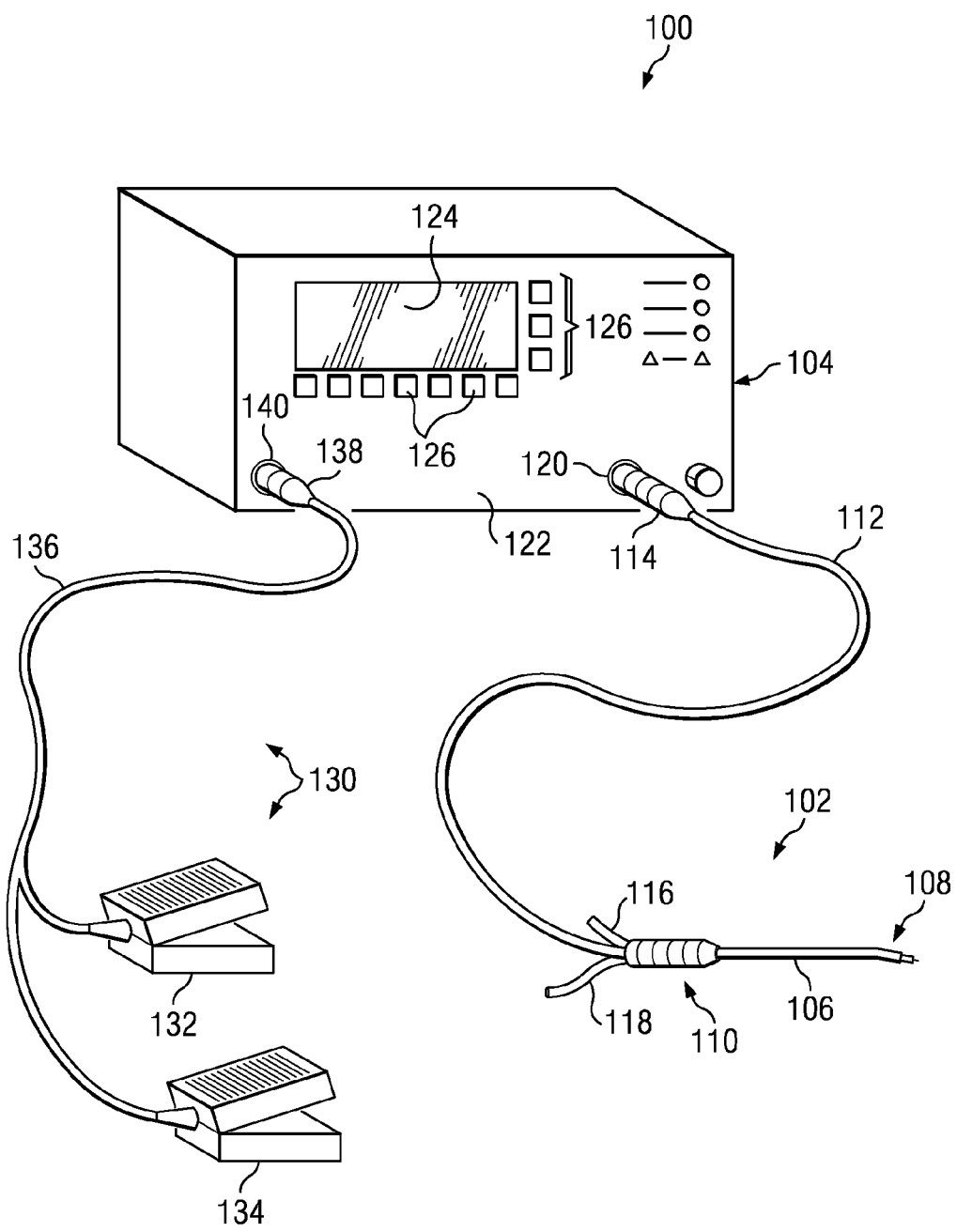
FIG. 1 shows an electrosurgical system in accordance with at least some embodiments.

Certain terms are used throughout the following description and claims to refer to particular system components. As one skilled in the art will appreciate, companies that design and manufacture electrosurgical systems may refer to a component by different names. This document does not intend to distinguish between components that differ in name but not function.

In the following discussion and in the claims, the terms "including" and "comprising" are used in an open-ended fashion, and thus should be interpreted to mean "including, but not limited to . . . " Also, the term "couple" or "couples" is intended to mean either an indirect or direct connection. Thus, if a first device couples to a second device, that connection may be through a direct connection or through an indirect electrical connection via other devices and connections.

Reference to a singular item includes the possibility that there are plural of the same items present. More specifically, as used herein and in the appended claims, the singular forms "a," "an," "said" and "the" include plural references unless the context clearly dictates otherwise. It is further noted that the claims may be drafted to exclude any optional element. As such, this statement serves as antecedent basis for use of such exclusive terminology as "solely," "only" and the like in connection with the recitation of claim elements, or use of a "negative" limitation. Lastly, it is to be appreciated that unless defined otherwise, all technical and scientific terms used herein have the same meaning as commonly understood by one of ordinary skill in the art to which this invention belongs.

"Active electrode" shall mean an electrode of an electrosurgical wand which produces an electrically-induced tissue-altering effect when brought into contact with, or close proximity to, a tissue targeted for treatment.

"Return electrode" shall mean an electrode of an electrosurgical wand which serves to provide a current flow path for electrons with respect to an active electrode, and/or an electrode of an electrical surgical wand which does not itself produce an electrically-induced tissue-altering effect on tissue targeted for treatment.

A fluid conduit said to be "within" an elongate shaft shall include not only a separate fluid conduit that physically resides within an internal volume of the elongate shaft, but also situations where the internal volume of the elongate shaft is itself the fluid conduit.

Where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

DETAILED DESCRIPTION

Before the various embodiments are described in detail, it is to be understood that this invention is not limited to particular variations set forth herein as various changes or modifications may be made, and equivalents may be substituted, without departing from the spirit and scope of the invention. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, many modifications may be made to adapt a particular situation, material, composition of matter, process, process act(s) or step(s) to the objective(s), spirit or scope of the present invention. All such modifications are intended to be within the scope of the claims made herein.

FIG. 1 illustrates an electrosurgical system 100 in accordance with at least some embodiments. In particular, the electrosurgical system comprises an electrosurgical wand 102 (hereinafter "wand") coupled to an electrosurgical controller 104 (hereinafter "controller"). The wand 102 comprises an elongate shaft 106 that defines distal end 108 where at least some electrodes are disposed. The elongate shaft 106 further defines a handle or proximal end 110, where a physician grips the wand 102 during surgical procedures. The wand 102 further comprises a flexible multi-conductor cable 112 housing a plurality of electrical leads (not specifically shown in FIG. 1), and the flexible multi-conductor cable 112 terminates in a wand connector 114. As shown in FIG. 1, the wand 102 couples to the controller 104, such as by a controller connector 120 on an outer surface 122 (in the illustrative case of FIG. 1, the front surface).

Though not visible in the view of FIG. 1, in some embodiments the wand 102 has one or more internal fluid conduits coupled to externally accessible tubular members. As illustrated, the wand 102 has a flexible tubular member 116 and a second flexible tubular member 118. In some embodiments, the flexible tubular member 116 is used to provide electrically conductive fluid (e.g., saline) to the distal end 108 of the wand. Likewise in some embodiments, flexible tubular member 118 is used to provide aspiration to the distal end 108 of the wand.

Still referring to FIG. 1, a display device or interface panel 124 is visible through the outer surface 122 of the controller 104, and in some embodiments a user may select operational modes of the controller 104 by way of the interface device 124 and related buttons 126.

In some embodiments the electrosurgical system 100 also comprises a foot pedal assembly 130. The foot pedal assembly 130 may comprise one or more pedal devices 132 and 134, a flexible multi-conductor cable 136 and a pedal connector 138. While only two pedal devices 132, 134 are shown, one or more pedal devices may be implemented. The outer surface 122 of the controller 104 may comprise a corresponding connector 140 that couples to the pedal connector 138. A physician may use the foot pedal assembly 130 to control various aspects of the controller 104, such as the operational mode. For example, a pedal device, such as pedal device 132, may be used for on-off control of the application of radio frequency (RF) energy to the wand 102, and more specifically for control of energy in an ablation mode. A second pedal device, such as pedal device 134, may be used to control and/or set the operational mode of the electrosurgical system. For example, actuation of pedal device 134 may switch between energy levels of an ablation mode.

The electrosurgical system 100 of the various embodiments may have a variety of operational modes. One such mode employs Coblation® technology. In particular, the assignee of the present disclosure is the owner of Coblation technology. Coblation technology involves the application of a radio frequency (RF) signal between one or more active electrodes and one or more return electrodes of the wand 102 to develop high electric field intensities in the vicinity of the target tissue. The electric field intensities may be sufficient to vaporize an electrically conductive fluid over at least a portion of the one or more active electrodes in the region between the one or more active electrodes and the target tissue. The electrically conductive fluid may be inherently present in the body, such as blood, or in some cases extracelluar or intracellular fluid. In other embodiments, the electrically conductive fluid may be a liquid or gas, such as isotonic saline. In some embodiments, such as surgical procedures on a disc between vertebrae, the electrically conductive fluid is delivered in the vicinity of the active electrode and/or to the target site by the wand 102, such as by way of the internal passage and flexible tubular member 116.

When the electrically conductive fluid is heated to the point that the atoms of the fluid vaporize faster than the atoms recondense, a gas is formed. When sufficient energy is applied to the gas, the atoms collide with each other causing a release of electrons in the process, and an ionized gas or plasma is formed (the so-called "fourth state of matter"). Stated otherwise, plasmas may be formed by heating a gas and ionizing the gas by driving an electric current through the gas, or by directing electromagnetic waves into the gas. The methods of plasma formation give energy to free electrons in the plasma directly, electron-atom collisions liberate more electrons, and the process cascades until the desired degree of ionization is achieved. A more complete description of plasma can be found in Plasma Physics, by R. J. Goldston and P. H. Rutherford of the Plasma Physics Laboratory of Princeton University (1995), the complete disclosure of which is incorporated herein by reference.

As the density of the plasma becomes sufficiently low (i.e., less than approximately 1020 atoms/cm$^3$ for aqueous solutions), the electron mean free path increases such that subsequently injected electrons cause impact ionization within the plasma. When the ionic particles in the plasma layer have sufficient energy (e.g., 3.5 electron-Volt (eV) to 5 eV), collisions of the ionic particles with molecules that make up the target tissue break molecular bonds of the target tissue, dissociating molecules into free radicals which then combine into gaseous or liquid species. Often, the electrons in the plasma carry the electrical current or absorb the electromagnetic waves and, therefore, are hotter than the ionic particles. Thus, the electrons, which are carried away from the target tissue toward the active or return electrodes, carry most of the plasma's heat, enabling the ionic particles to break apart the target tissue molecules in a substantially non-thermal manner.

By means of the molecular dissociation (as opposed to thermal evaporation or carbonization), the target tissue is volumetrically removed through molecular dissociation of larger organic molecules into smaller molecules and/or atoms, such as hydrogen, oxygen, oxides of carbon, hydrocarbons and nitrogen compounds. The molecular dissociation completely removes the tissue structure, as opposed to dehydrating the tissue material by the removal of liquid within the cells of the tissue and extracellular fluids, as occurs in related art electrosurgical desiccation and vaporization. A more detailed description of the molecular dissociation can be found in commonly assigned U.S. Pat. No. 5,697,882, the complete disclosure of which is incorporated herein by reference.

In addition to the Coblation mode, the electrosurgical system 100 of FIG. 1 may also in particular situations be useful for sealing larger arterial vessels (e.g., on the order of about 1 mm in diameter), when used in what is known as a coagulation mode. Thus, the system of FIG. 1 may have an ablation mode where RF energy at a first voltage is applied to one or more active electrodes sufficient to effect molecular dissociation or disintegration of the tissue, and the system of FIG. 1 may have a coagulation mode where RF energy at a second, lower voltage is applied to one or more active electrodes (either the same or different electrode(s) as the ablation mode) sufficient to heat, shrink, seal, fuse, and/or achieve homeostasis of severed vessels within the tissue.

The energy density produced by electrosurgical system 100 at the distal end 108 of the wand 102 may be varied by adjusting a variety of factors, such as: the number of active electrodes; electrode size and spacing; electrode surface area; asperities and/or sharp edges on the electrode surfaces; electrode materials; applied voltage; current limiting of one or more electrodes (e.g., by placing an inductor in series with an electrode); electrical conductivity of the fluid in contact with the electrodes; density of the conductive fluid; and other factors. Accordingly, these factors can be manipulated to control the energy level of the excited electrons. Because different tissue structures have different molecular bonds, the electrosurgical system 100 may be configured to produce energy sufficient to break the molecular bonds of certain tissue but insufficient to break the molecular bonds of other tissue. For example, fatty tissue (e.g., adipose) has double bonds that require an energy level higher than 4 eV to 5 eV (i.e., on the order of about 8 eV) to break. Accordingly, the Coblation® technology in some operational modes does not ablate such fatty tissue; however, the Coblation® technology at the lower energy levels may be used to effectively ablate cells to release the inner fat content in a liquid form. Other modes may have increased energy such that the double bonds can also be broken in a similar fashion as the single bonds (e.g., increasing voltage or changing the electrode configuration to increase the current density at the electrodes).

A more complete description of the various phenomena can be found in commonly assigned U.S. Pat. Nos. 6,355,032; 6,149,120 and 6,296,136, the complete disclosures of which are incorporated herein by reference.

Figure 2A:
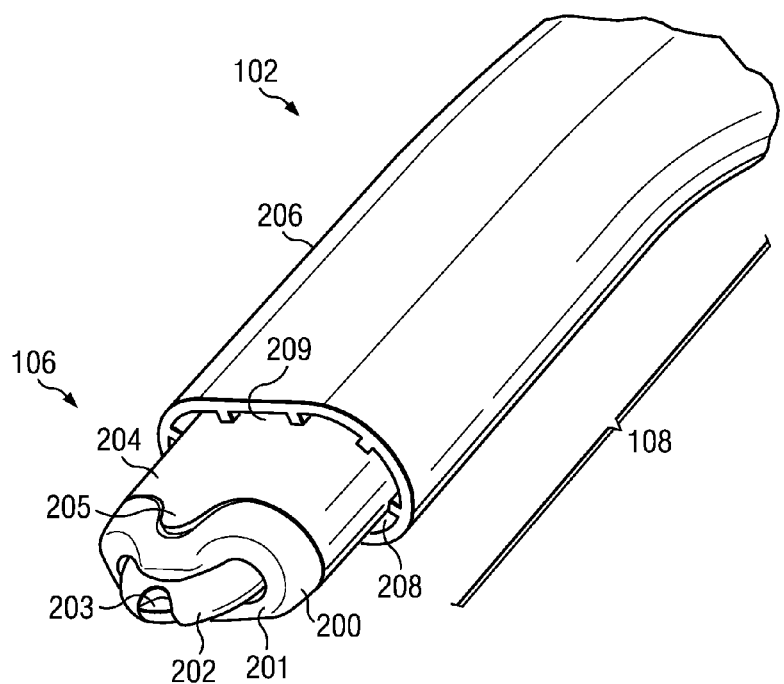
FIG. 2A shows a perspective view a portion of a wand in accordance with at least some embodiments.

FIG. 2A illustrates a perspective view of the distal end 108 of wand 102 in accordance with at least some embodiments. In some embodiments, a portion of the elongate shaft 106 may be made of a metallic material (e.g., Grade TP304 stainless steel hypodermic tubing). In other embodiments, portions of the elongate shaft may be constructed of other suitable materials, such as inorganic insulating materials. The elongate shaft 106 may define a circular cross-section at the handle or proximal end 110 (not shown in FIG. 2), and at least a portion of the distal end 108 may be flattened to define an elliptical or semi-circular cross-section.

In embodiments where the elongate shaft is metallic, the distal end 108 may further comprise a non-conductive spacer 200 coupled to the elongate shaft 106. In some cases the spacer 200 is ceramic, but other non-conductive materials resistant to degradation when exposed to plasma may be equivalently used (e.g., glass). The spacer 200 supports electrodes of conductive material, with illustrative active electrode labeled 202 in FIG. 2A. Active electrode 202 defines an exposed surface area of conductive material, where active electrode 202 is a loop of wire of particular diameter. For embodiments using a loop of wire, the loop of wire may be molybdenum or tungsten having a diameter between and including 0.025 and 0.035 inches, and more preferably of 0.030 inches, and having an exposed standoff distance away from the spacer 200 of approximately 0.080 inches. Spacer 200 may have a step feature 201 that serves to limit the depth of penetration of active electrode 202 by providing a non-conductive surface to rest on adjacent tissue, thereby allowing for a more controlled and precise cut as well as providing for a more uniform depth of thermal effect in tissue. Further, spacer 200 may define an elliptical or semi-circular cross-section to provide a flattened support profile for active electrode 202.

Figure 2B:
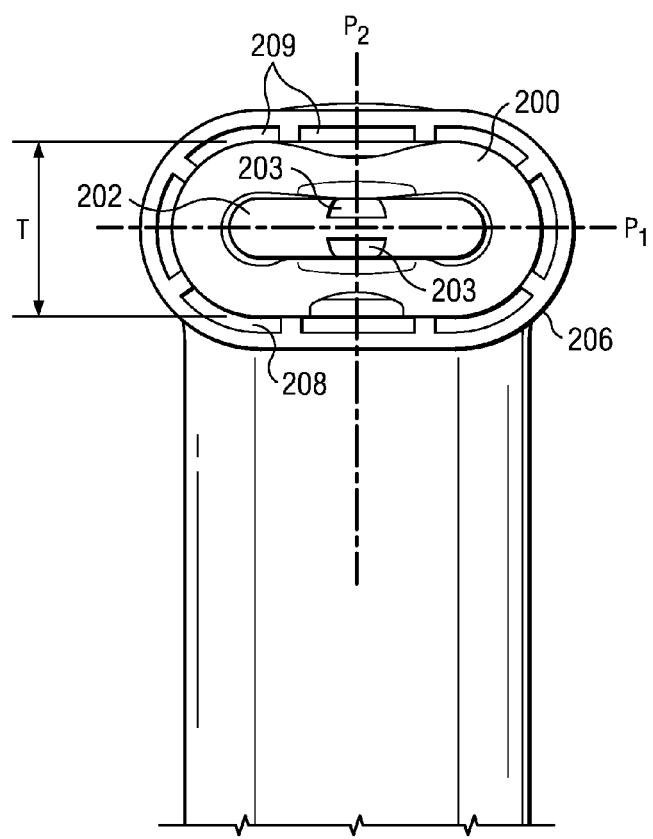
FIG. 2B shows an end elevation view of a wand in accordance with at least some embodiments.
Figure 2C:
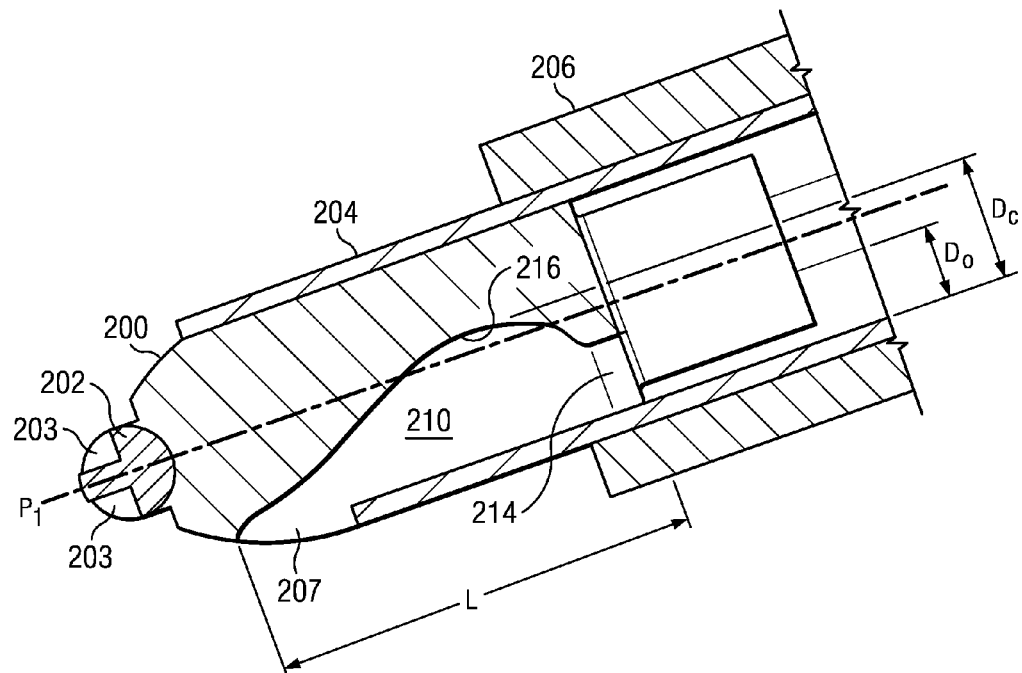
FIG. 2C shows a cross-sectional view of a wand in accordance with at least some embodiments.
Figure 3A:
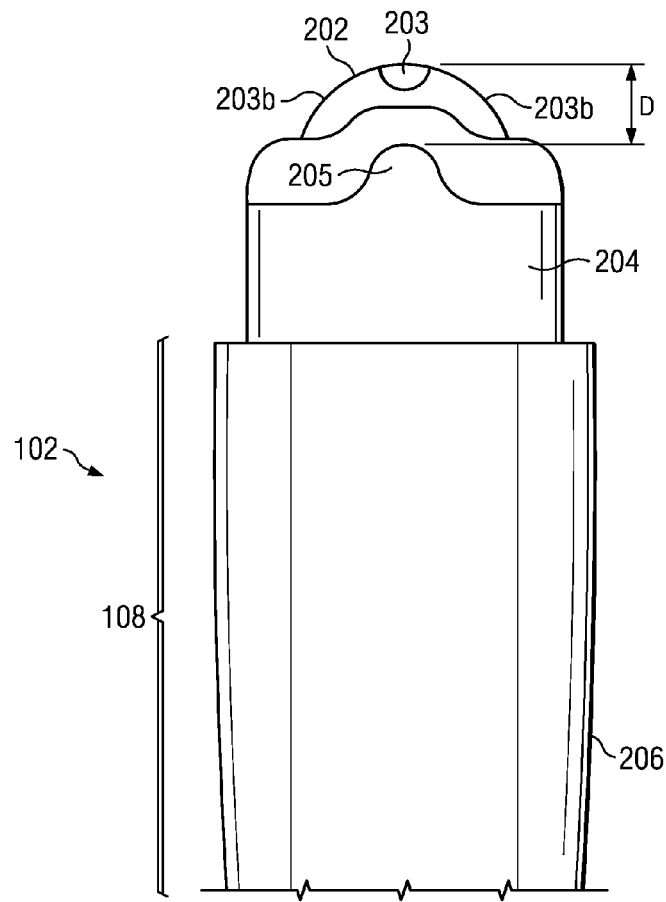
FIG. 3A shows a side elevation view of a wand in accordance with at least some embodiments.
Figure 3B:
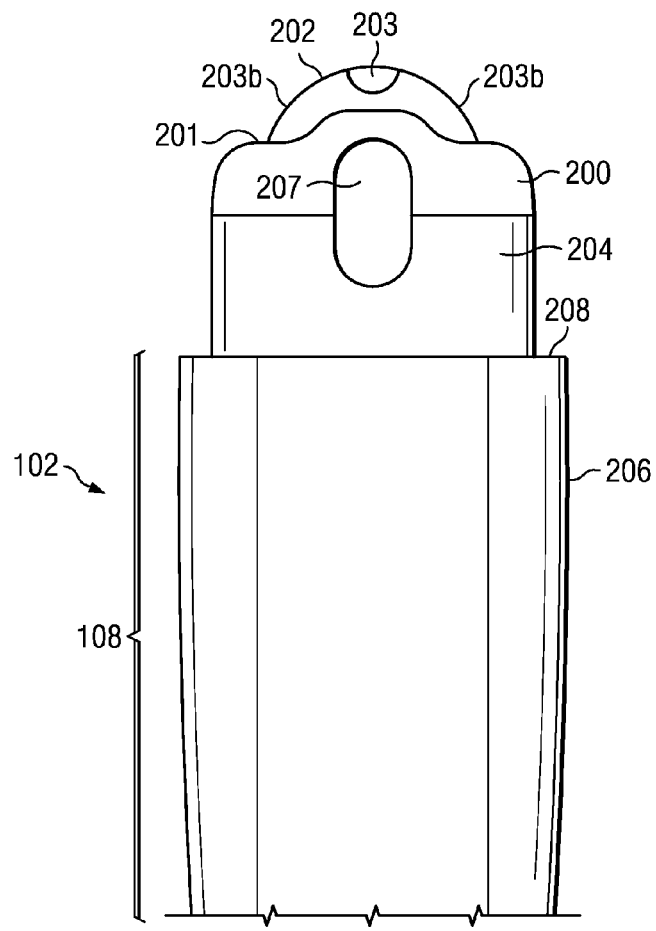
FIG. 3B shows a side elevation view of a wand in accordance with at least some embodiments.

In certain embodiments, the active electrode has an edge feature 203 at a specific, distinct location advantageous for enhanced plasma formation. In particular, active electrode 202 may be defined by an edge feature 203 (e.g., a scalloped portion, a cut, divot, or asperity) having a cut diameter and depth between and including 0.008 and 0.0012 inches, and more preferably of approximately 0.010 inches on each side, leaving a thin segment of approximately 0.010 inches thickness in the central portion of active electrode 202. Referring to FIG. 2B, edge feature 203 is preferably located in at least two positions on opposed sides of a plane $P_1$ bisecting the wire diameter of active electrode 202, and centered about a second plane $P_2$ bisecting the width of active electrode 202. FIG. 2C shows a cross-sectional view of active electrode 202 and spacer 200 taken substantially along plane $P_2$ of FIG. 2B. In particular, FIG. 2C shows the orientation of edge feature 203 in an embodiment where the feature is a pair of symmetric cuts in active electrode 202. In certain other embodiments contemplated but not shown, edge feature 203 can also be a protruding section along active electrode 202 formed through a coining, welding, or other forming operation to provide exterior edges for improved localized plasma formation in these areas. Edge feature 203 at the distal tip of active electrode 202 helps initiate localized plasma formation in the relative center of active electrode 202 for smooth cutting. Referring briefly to FIGS. 3A and 3B, active electrode 202 further has rounded edges or a smooth feature 203b at a second, distinct location away from edge feature 203 for conductive/resistive heating of tissue at locations spaced away from edge feature 203. In particular, active electrode 202 may be loop of wire characterized by edge feature 203 at the apex of the loop and smooth feature 203b adjacent to edge feature 203 and disposed on either side of the loop forming active electrode 202. This conductive heating of surrounding tissue helps provide concomitant hemostasis of small blood vessels while plasma is initiated for cutting.

Referring again to FIG. 2A, wand 102 includes a return electrode 204 for completing the current path between active electrode 202 and controller 104. Return electrode 204 is preferably a semi-annular member defining the exterior of shaft 106, and a distal portion of return electrode 204 is preferably exposed. Return electrode 204 is suitably connected to controller 104. At least a proximal portion of return electrode 204 is disposed within an electrically insulative sheath 206, which is typically formed as one or more electrically insulative sheaths or coatings, such as polytetrafluoroethylene, polyimide, and the like. The provision of the electrically insulative sheath 206 encircling over a portion of return electrode 204 prevents direct electrical contact between return electrode 204 and any adjacent body structure or the surgeon. Such direct electrical contact between a body structure (e.g., tendon) and an exposed common electrode member 204 could result in unwanted heating and necrosis of the structure at the point of contact causing necrosis.

Return electrode 204 is preferably formed from an electrically conductive material, usually metal, which is selected from the group consisting of stainless steel alloys, platinum or its alloys, titanium or its alloys, molybdenum or its alloys, and nickel or its alloys. Referring now to FIG. 3A, the distance D between active electrode 202 and return electrode 204 is preferably kept substantially constant. As such, it is preferred that the distal projection of return electrode 204 have a non-uniform shape to approximate the geometry of active electrode 202. In a preferred embodiment, return electrode 204 has an extended feature in the form of tab 205 extending distally. This extension tab 205 maintains a near-uniform distance between the active loop electrode 202 and return electrode 204. Preferably, the extended tab 205 closes the distance between the return electrode 204 and the active electrode 202 as measured at the apex of the active loop electrode 202, thereby keeping the distance D between all portions of the active and return electrodes substantially constant. It also brings the distal end of the return electrode 204 closer to the targeted tissue to improve the conduction of current through tissue and saline between the active and return electrodes. This enables a more uniform and continuous delivery of electrical current through the targeted tissue during coagulation mode, providing greater depth of thermal penetration for improved coagulation of blood vessels.

In some embodiments saline is delivered to the distal end 108 of wand, possibly to aid in plasma creation. Referring again to FIGS. 2A and 2B, discharge apertures 208 are illustrated on the distal end 108 spaced proximally from return electrode 204. Discharge apertures 208 are formed at the distal most point of the insulative sheath 206 encircling a portion of return electrode 204. Insulative sheath 206 further creates an annular gap between the insulative sheath and return electrode 204, in which multiple axially disposed ribs are spaced equally throughout to form a plurality of fluid flow channels 209 that direct discharged conductive fluid toward the return electrode 204 and active electrode 202. Discharge apertures 208 characterize the distal most opening of the associated plurality of flow channels 209. In the particular embodiment illustrated, eight discharge apertures are shown, but fewer or greater numbers of discharge apertures are contemplated. The discharge apertures 208 are fluidly coupled to the flexible tubular member 116 (FIG. 1) by way of a fluid conduit within the wand 102. Thus, saline or other fluid may be pumped into the flexible tubular member 116 (FIG. 1) and discharged through the plurality of fluid flow channels 209 and discharge apertures 208 to further aid in developing consistent wetting around the circumference of return electrode 204.

In yet still further embodiments, aspiration is provided at the distal end 108 of the wand 102. FIG. 3B illustrates aspiration aperture 207 (i.e., suction port 207) at the distal end 108 of the device and disposed through the non-conductive spacer 200 and defining in part an opening in return electrode 204. Suction port 207 is disposed at distal end 108 and in certain embodiments preferably only located on one side of spacer 200 and disposed on an inferior surface of spacer 200 (such that when in use the suction port 207 is preferably disposed inferiorly with regard to the angle of approach to the target tissue), and accordingly may be disposed on the opposite side of spacer 200 from tab 205. Suction port 207 aspirates the area near the distal end 108, such as to remove excess fluids and remnants of ablation. The location of suction port 207 further provides for ample wetting of the active and return electrodes on the opposing side of the tip, with the saline flowing down from discharge apertures 208 on the non-suction side of the shaft, around the active electrode tip, then pulled back up on the inferior side of the wand with suction port 207. Applicants have found it is particularly beneficial to direct conductive fluid flow to discrete areas away from the suction port 207 to provide broader wetting of the exposed surface of return electrode 204, enabling more uniform plasma formation.

Figure 3C:
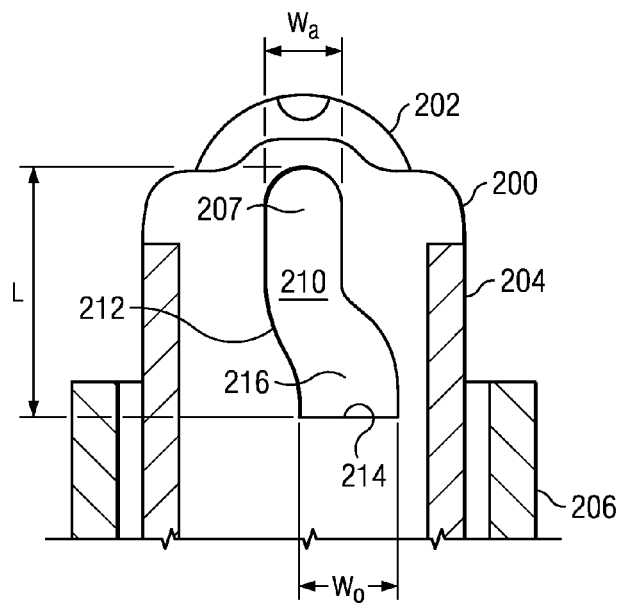
FIG. 3C shows a cross-sectional view of a wand in accordance with at least some embodiments.

Additionally, referring briefly to both FIGS. 2B and 3B, suction port 207 may be offset inferior from plane $P_1$, which also bisects the thickness T of distal end 108 of elongate shaft 106. FIG. 3C shows a cross-section view taken substantially along plane $P_1$ of FIG. 2B. In particular, FIG. 3C shows suction port 207 as well as spacer fluid conduit 210 defined by walls 212. Fluid conduit 210 further comprises an aspiration chamber 216 having a fluid conduit opening 214. In operation, suction is provided to the flexible tubular member 118 (FIG. 1), and flexible tubular member 118 either extends into the internal volume of the wand 102 to become, or fluidly couples to, opening 214 of aspiration chamber 216. Thus, conductive fluid, molecularly dissociated tissue, as well as tissue pieces are drawn through the suction port 207, into the fluid conduit 210, and eventually through aspiration chamber 216 and opening 214. Aspiration chamber 216 is spaced proximally from suction port 207, and the inventors of the present specification have found that a particular depth of aspiration chamber 216 and width of opening 214 work better than others. For example, without the increased area of aspiration chamber 216, the fluid conduit 210 may be subject to clogging. Likewise, if the coupling point for flexible tubular member 118 at opening 114 does not have an increased diameter, clogging may occur. In accordance with at least some embodiments, the nature of fluid conduit 210 transitions over a length L between suction port 207 and opening 214. The entrance to the fluid conduit 210 is referenced by an aspiration aperture width $W_a$. In accordance with at least some embodiments the internal walls 212 that define fluid conduit 210 smoothly transition to a change in width referenced by an opening width $W_o$ at opening 214 over length L wherein the width change to $W_o$ at opening 214 should be at least half the full ID of the shaft. Additionally, referring again now to FIG. 2C, the depth of fluid conduit 210 as it transitions to aspiration chamber 216 should smoothly vary at least to a depth referenced by depth $D_c$, wherein the apex of depth $D_c$ should be at least half the thickness T (FIG. 2B) of spacer 200 and then smoothly transitioning to a depth $D_o$ at opening 214. The inventors present the nature of fluid conduit 210 as described above by way of example only. Other variances and transitions in the shape, respective widths, and depths of portions of fluid conduit 210 and aspiration chamber 216 from suction port 207 to opening 214 may be equivalently used.

As shown for example in FIGS. 2A-3B, return electrode 204 is not directly connected to active electrode 202. To complete a current path so that active electrode 202 is electrically connected to return electrode 204 in the presence of a target tissue, electrically conducting liquid (e.g., isotonic saline) is caused to flow along liquid paths emanating from discharge apertures 208 and contacting both return electrode 204 and active electrode 202. When a voltage difference is applied between active electrode 202 and return electrode 204, high electric field intensities will be generated at the distal tip of active electrode 202 with current flow from active electrode 202 to the return electrode 204, the high electric field intensities causing ablation of target tissue adjacent the distal tip of active electrode 202.

FIG. 4A shows a cross-sectional elevation view of a wand 102 in accordance with at least some embodiments. In particular, FIG. 4 shows the handle or proximal end 110 coupled to the elongate shaft 106. As illustrated, the elongate shaft 106 telescopes within the handle, but other mechanisms to couple the elongate shaft to the handle may be equivalently used. The elongate shaft 106 defines internal conduit 400 that serves several purposes. For example, in the embodiments illustrated by FIG. 4 the electrical leads 402 and 404 extend through the internal conduit 400 to electrically couple to the active electrode 202 and return electrode 204, respectively. Likewise, the flexible tubular member 116 extends through the internal conduit 400 to fluidly couple to the plurality of flow channels 209 and discharge apertures 208 via insulative sheath 206.

The internal conduit 400 also serves as the aspiration route. In particular, FIG. 4B illustrates suction port 207. In the embodiments illustrated the flexible tubular member 118, through which aspiration is performed, couples through the handle and then fluidly couples to the internal conduit 400. Thus, the suction provided through flexible tubular member 118 provides aspiration at the suction port 207. The fluids that are drawn into the internal fluid conduit 400 may abut the portion of the flexible tubular member 116 that resides within the internal conduit as the fluids are drawn along the conduit; however, the flexible tubular member 116 is sealed, and thus the aspirated fluids do not mix with the fluid (e.g., saline) being pumped through the flexible tubular member 116. Likewise, the fluids that are drawn into the internal fluid conduit 400 may abut portions of the electrical leads 402 and 404 within the internal fluid conduit 400 as the fluids are drawn along the conduit. However, the electrical leads are insulated with an insulating material that electrically and fluidly isolates the leads from any substance within the internal fluid conduit 400. Thus, the internal fluid conduit serves, in the embodiments shown, two purposes—one to be the pathway through which the flexible tubular member 116 and electrical leads traverse to reach the distal end 108, and also as the conduit through which aspiration takes place. In other embodiments, the flexible tubular member 118 may extend partially or fully through the elongate shaft 106, and thus more directly couple to the aspiration apertures.

FIGS. 4A and 4B also illustrate that, in accordance with at least some embodiments, a portion of the elongate shaft 106 is circular (e.g., portion 410) and another portion of the elongate shaft 106 is flattened (e.g., portion 412) to define an elliptical or semi-circular cross-section. In some embodiments, the distal 3 centimeters or less is flattened, and in some cases the last 2 centimeters. In other embodiments, the entire elongate shaft may define the elliptical or semi-circular cross-section. Additionally, in the particular embodiments illustrated the angle between the axis of portion 410 and the axis of portion 412 is non-zero, and in some embodiments the acute angle between the axis of portion 410 and the axis of portion 412 is 20 degrees, but greater or lesser angles may be equivalently used.

Figure 5:
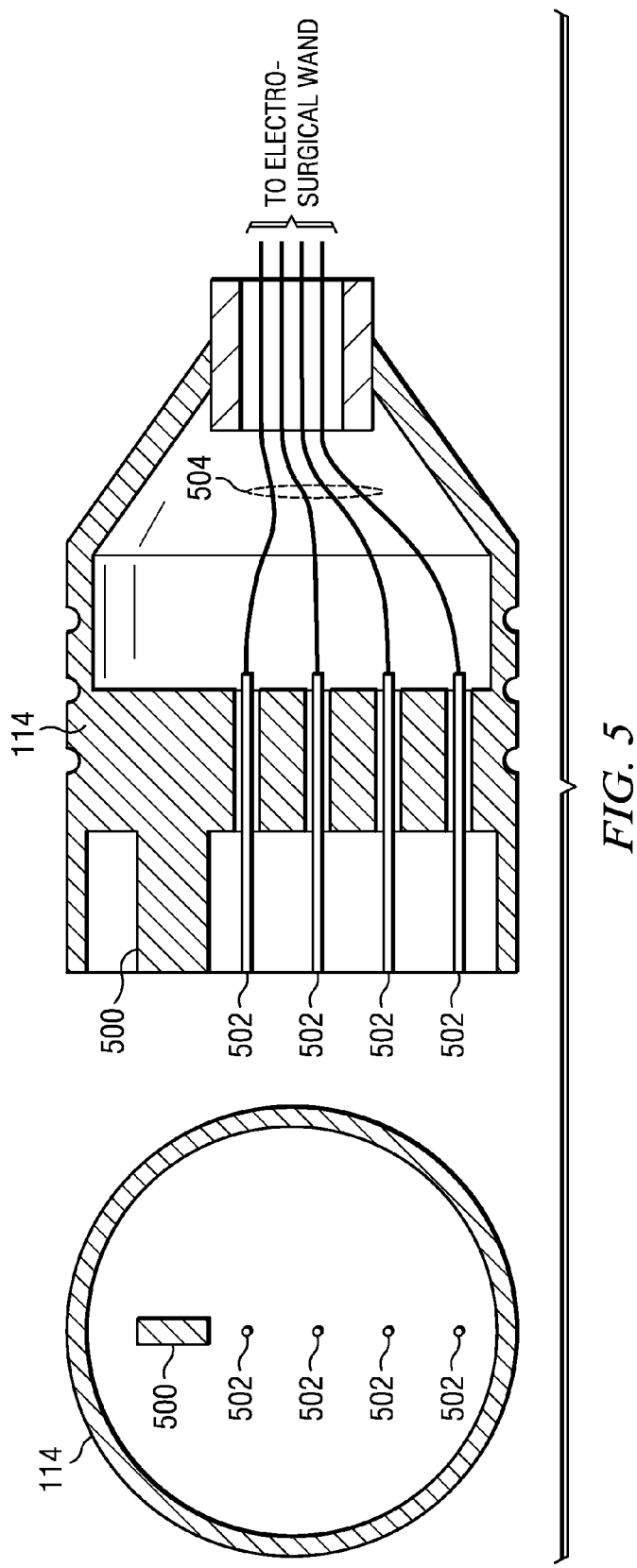
FIG. 5 shows both an elevational end-view (left) and a cross-sectional view (right) of a wand connector in accordance with at least some embodiments.

As illustrated in FIG. 1, flexible multi-conductor cable 112 (and more particularly its constituent electrical leads 402, 404 and possibly others) couple to the wand connector 114. Wand connector 114 couples the controller 104, and more particularly the controller connector 120. FIG. 5 shows both a cross-sectional view (right) and an end elevation view (left) of wand connector 114 in accordance with at least some embodiments. In particular, wand connector 114 comprises a tab 500. Tab 500 works in conjunction with a slot on controller connector 120 (shown in FIG. 6) to ensure that the wand connector 114 and controller connector 120 only couple in one relative orientation. The illustrative wand connector 114 further comprises a plurality of electrical pins 502 protruding from wand connector 114. In many cases, the electrical pins 502 are coupled one each to an electrical lead of electrical leads 504 (two of which may be leads 402 and 404 of FIG. 4). Stated otherwise, in particular embodiments each electrical pin 502 couples to a single electrical lead, and thus each illustrative electrical pin 502 couples to a single electrode of the wand 102. In other cases, a single electrical pin 502 couples to multiple electrodes on the electrosurgical wand 102. While FIG. 5 shows four illustrative electrical pins, in some embodiments as few as two electrical pins, and as many as 26 electrical pins, may be present in the wand connector 114.

Figure 6:
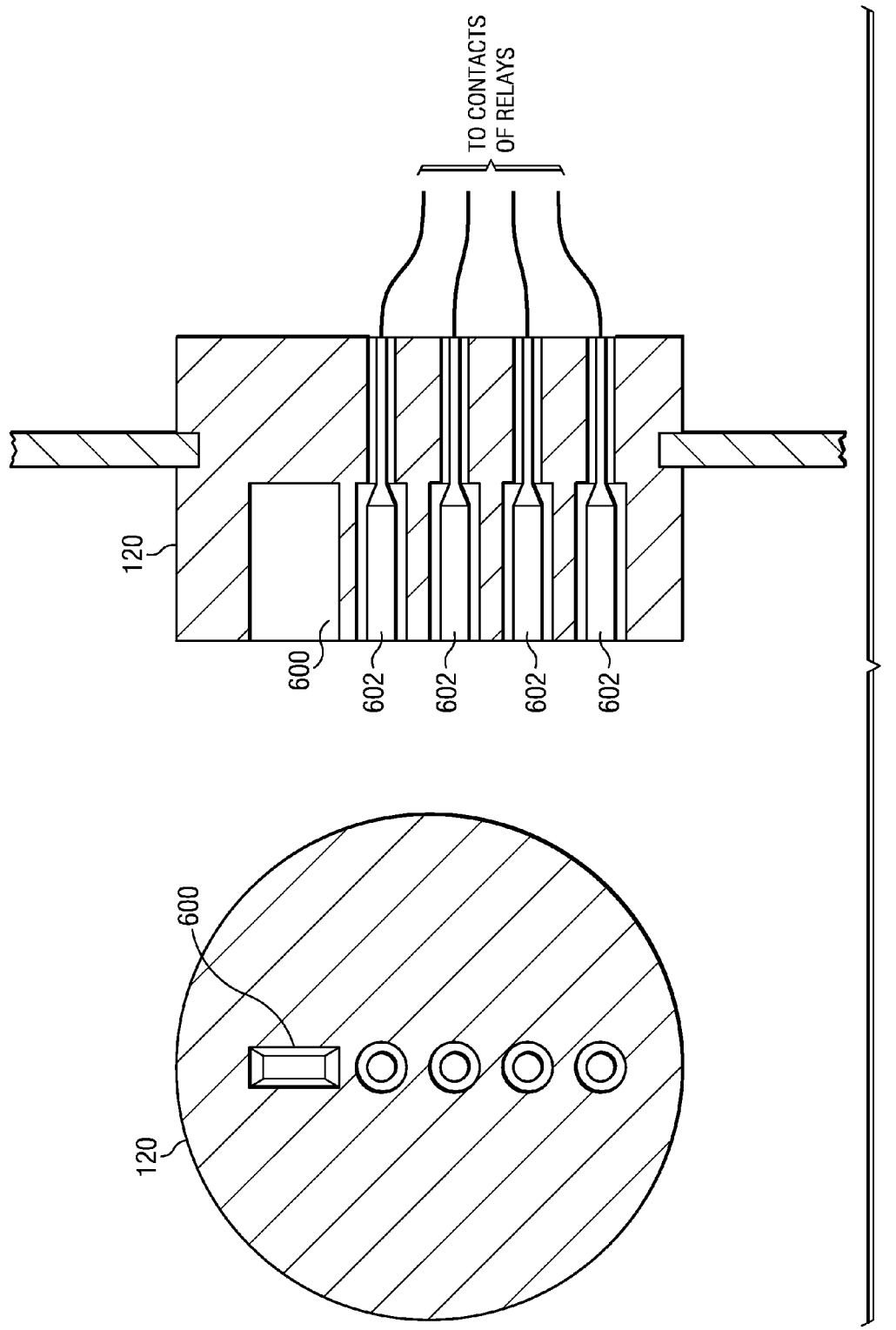
FIG. 6 shows both an elevational end-view (left) and a cross-sectional view (right) of a controller connector in accordance with at least some embodiments.

FIG. 6 shows both a cross-sectional view (right) and an end elevation view (left) of controller connector 120 in accordance with at least some embodiments. In particular, controller connector 120 comprises a slot 600. Slot 600 works in conjunction with a tab 500 on wand connector 114 (shown in FIG. 5) to ensure that the wand connector 114 and controller connector 120 only couple in one orientation. The illustrative controller connector 120 further comprises a plurality of electrical pins 602 residing within respective holes of controller connector 120. The electrical pins 602 are coupled to terminals of a voltage generator within the controller 104 (discussed more thoroughly below). When wand connector 114 and controller connector 120 are coupled, each electrical pin 602 couples to a single electrical pin 502. While FIG. 6 shows only four illustrative electrical pins, in some embodiments as few as two electrical pins, and as many as 26 electrical pins may be present in the wand connector 120.

While illustrative wand connector 114 is shown to have the tab 500 and male electrical pins 502, and controller connector 120 is shown to have the slot 600 and female electrical pins 602, in alternative embodiments the wand connector has the female electrical pins and slot, and the controller connector 120 has the tab and male electrical pins, or other combination. In other embodiments, the arrangement of the pins within the connectors may enable only a single orientation for connection of the connectors, and thus the tab and slot arrangement may be omitted. In yet still other embodiments, other mechanical arrangements to ensure the wand connector and controller connector couple in only one orientation may be equivalently used. In the case of a wand with only two electrodes, and which electrodes may be either active or return electrodes as the physical situation dictates, there may be no need to ensure the connectors couple in a particular orientation.

Figure 7:
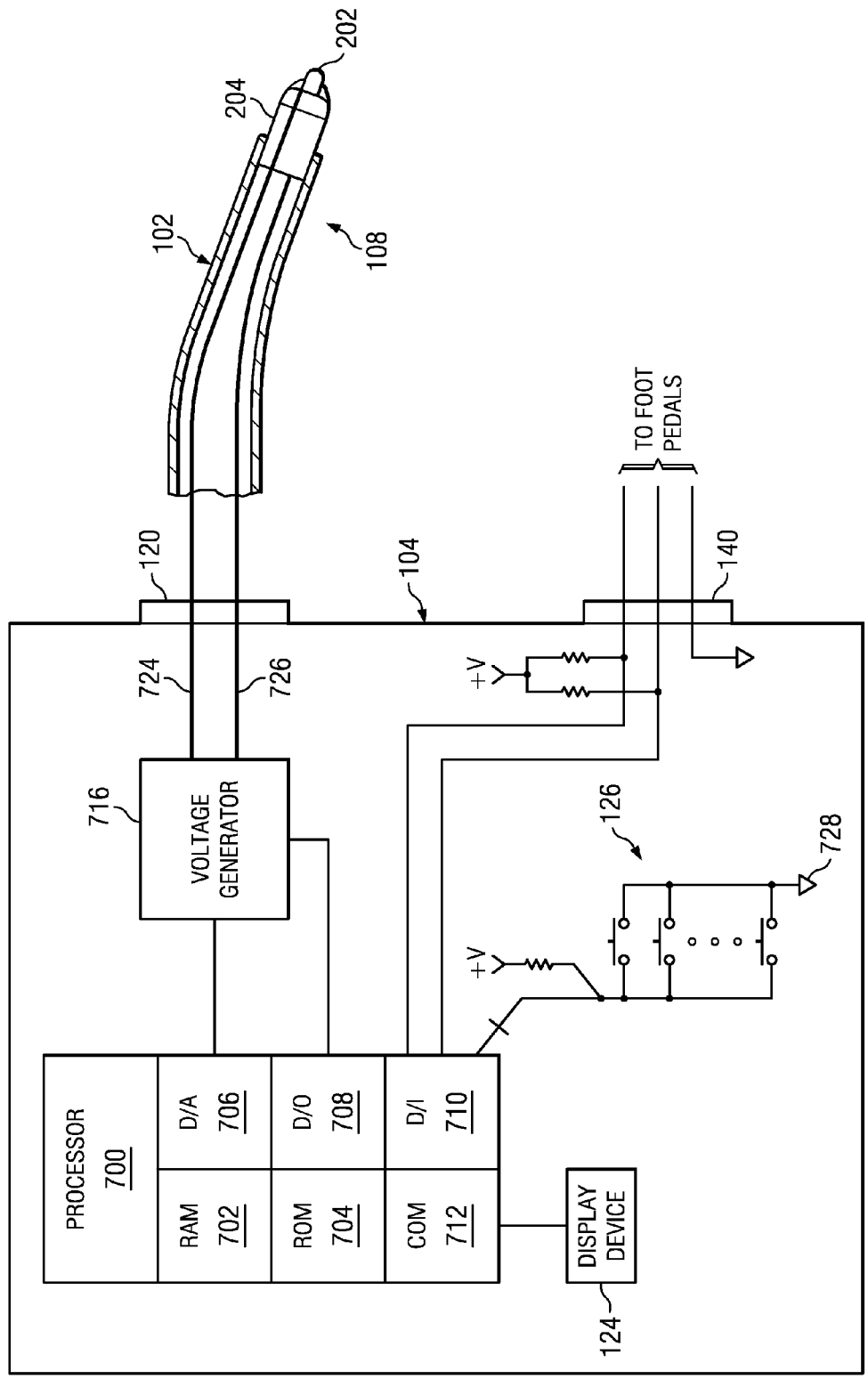
FIG. 7 shows an electrical block diagram of an electrosurgical controller in accordance with at least some embodiments.

FIG. 7 illustrates a controller 104 in accordance with at least some embodiments. In particular, the controller 104 comprises a processor 700. The processor 700 may be a microcontroller, and therefore the microcontroller may be integral with random access memory (RAM) 702, read-only memory (RAM) 704, digital-to-analog converter (D/A) 706, digital outputs (D/O) 708 and digital inputs (D/I) 710. The processor 700 may further provide one or more externally available peripheral busses, such as a serial bus (e.g., I$^2$C), parallel bus, or other bus and corresponding communication mode. The processor 700 may further be integral with a communication logic 712 to enable the processor 700 to communicate with external devices, as well as internal devices, such as display device 124. Although in some embodiments the controller 104 may implement a microcontroller, in yet other embodiments the processor 700 may be implemented as a standalone central processing unit in combination with individual RAM, ROM, communication, D/A, D/O and D/I devices, as well as communication port hardware for communication to peripheral components.

ROM 704 stores instructions executable by the processor 700. In particular, the ROM 704 may comprise a software program that implements the various embodiments of periodically reducing voltage generator output to change position of the plasma relative to the electrodes of the wand (discussed more below), as well as interfacing with the user by way of the display device 124 and/or the foot pedal assembly 130 (FIG. 1). The RAM 702 may be the working memory for the processor 700, where data may be temporarily stored and from which instructions may be executed. Processor 700 couples to other devices within the controller 104 by way of the D/A converter 706 (e.g., the voltage generator 716), digital outputs 708 (e.g., the voltage generator 716), digital inputs 710 (i.e., push button switches 126, and the foot pedal assembly 130 (FIG. 1)), and other peripheral devices.

Voltage generator 716 generates selectable alternating current (AC) voltages that are applied to the electrodes of the wand 102. In the various embodiments, the voltage generator defines two terminals 724 and 726. In accordance with the various embodiments, the voltage generator generates an alternating current (AC) voltage across the terminals 724 and 726. In at least some embodiments the voltage generator 716 is electrically "floated" from the balance of the supply power in the controller 104, and thus the voltage on terminals 724, 726, when measured with respect to the earth ground or common (e.g., common 728) within the controller 104, may or may not show a voltage difference even when the voltage generator 716 is active.

The voltage generated and applied between the active terminal 724 and return terminal 726 by the voltage generator 716 is a RF signal that, in some embodiments, has a frequency of between about 5 kilo-Hertz (kHz) and 20 Mega-Hertz (MHz), in some cases being between about 30 kHz and 2.5 MHz, often between about 100 kHz and 200 kHz. In applications associated with otolaryngology-head and neck procedures, a frequency of about 100 kHz appears most effective. The RMS (root mean square) voltage generated by the voltage generator 716 may be in the range from about 5 Volts (V) to 1000 V, preferably being in the range from about 10 V to 500 V, often between about 100 V to 350 V depending on the active electrode size and the operating frequency. The peak-to-peak voltage generated by the voltage generator 716 for ablation or cutting in some embodiments is a square wave form in the range of 10 V to 2000 V and in some cases in the range of 100 V to 1800 V and in other cases in the range of about 28 V to 1200 V, often in the range of about 100 V to 320 V peak-to-peak (again, depending on the electrode size and the operating frequency).

Still referring to the voltage generator 716, the voltage generator 716 delivers average power levels ranging from several milliwatts to hundreds of watts per electrode, depending on the voltage applied for the target tissue being treated, and/or the maximum allowed temperature selected for the wand 102. The voltage generator 716 is configured to enable a user to select the voltage level according to the specific requirements of a particular procedure. A description of one suitable voltage generator 716 can be found in commonly assigned U.S. Pat. Nos. 6,142,992 and 6,235,020, the complete disclosure of both patents are incorporated herein by reference for all purposes.

In some embodiments, the various operational modes of the voltage generator 716 may be controlled by way of digital-to-analog converter 706. That is, for example, the processor 700 may control the output voltage by providing a variable voltage to the voltage generator 716, where the voltage provided is proportional to the voltage generated by the voltage generator 716. In other embodiments, the processor 700 may communicate with the voltage generator by way of one or more digital output signals from the digital output 708 device, or by way of packet based communications using the communication device 712 (connection not specifically shown so as not to unduly complicate FIG. 8).

FIG. 7 also shows a simplified side view of the distal end 108 of the wand 102. As shown, illustrative active electrode 202 of the wand 102 electrically couples to terminal 724 of the voltage generator 716 by way of the connector 120, and return electrode 204 electrically couples to terminal 726 of the voltage generator 716.

Figure 8:
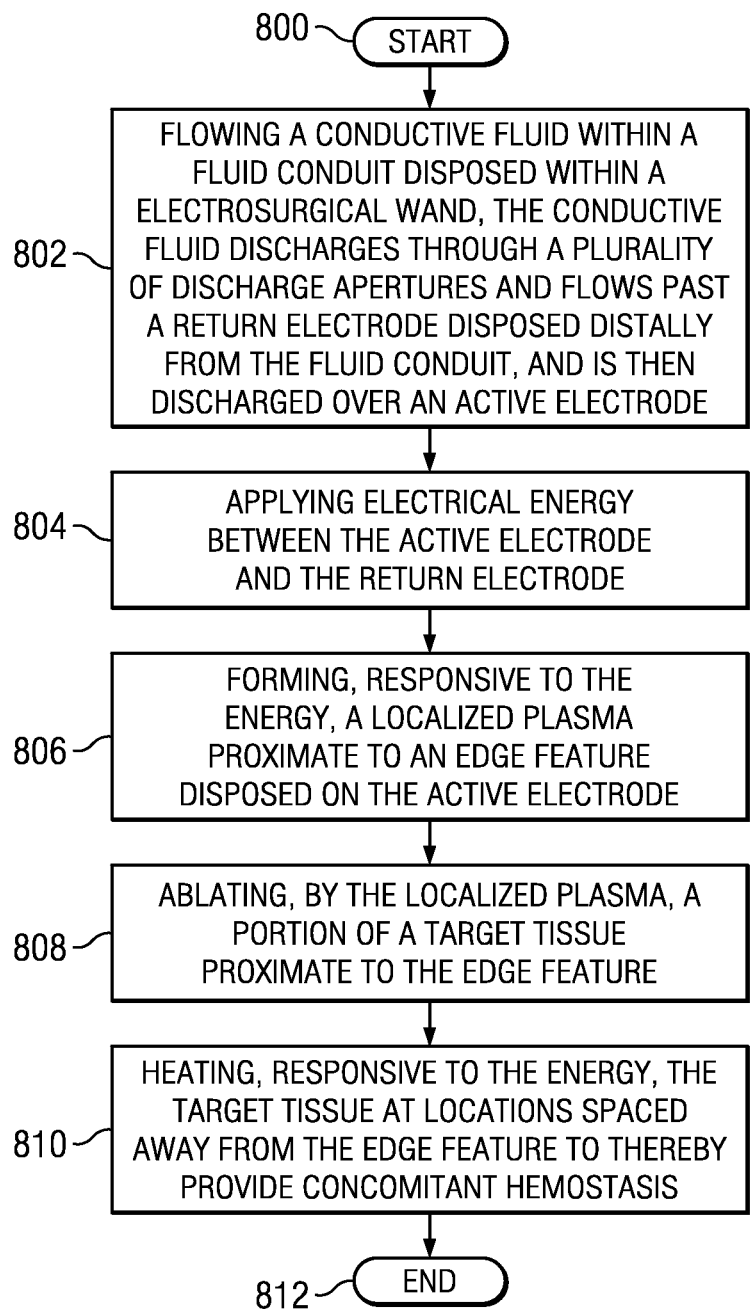
FIG. 8 shows a method in accordance with at least some embodiments.

FIG. 8 shows a method in accordance with at least some embodiments. In particular, the method starts (block 800) and proceed to: flowing a conductive fluid within a fluid conduit disposed within a electrosurgical wand, the conductive fluid discharges through a plurality of discharge apertures and flows past a return electrode disposed distally from the fluid conduit, and is then discharged over an active electrode (block 802); applying electrical energy between the active electrode and the return electrode (block 804); forming, responsive to the energy, a localized plasma proximate to an edge feature disposed on the active electrode (block 806); ablating, by the localized plasma, a portion of a target tissue proximate to the edge feature (block 808); and heating, responsive to the energy, the target tissue at locations spaced away from the edge feature to thereby provide concomitant hemostasis (block 810). And thereafter the method ends (block 812).

The above discussion is meant to be illustrative of the principles and various embodiments of the present invention. Numerous variations and modifications possible. For example, while in some cases electrodes were designated as upper electrodes and lower electrodes, such a designation was for purposes of discussion, and shall not be read to require any relationship to gravity during surgical procedures. It is intended that the following claims be interpreted to embrace all such variations and modifications.

While preferred embodiments of this disclosure have been shown and described, modifications thereof can be made by one skilled in the art without departing from the scope or teaching herein. The embodiments described herein are exemplary only and are not limiting. Because many varying and different embodiments may be made within the scope of the present inventive concept, including equivalent structures, materials, or methods hereafter though of, and because many modifications may be made in the embodiments herein detailed in accordance with the descriptive requirements of the law, it is to be understood that the details herein are to be interpreted as illustrative and not in a limiting sense.

What is claimed is:

1. An electrosurgical wand comprising:
an elongate shaft that defines a handle end and a distal end, the distal end defining a thickness;
a connector comprising a first and second electrical pins;
an insulative sheath characterized by a plurality of discharge apertures on the distal end of the elongate shaft, the plurality of discharge apertures fluidly coupled to a first fluid conduit, and the first fluid conduit within the elongate shaft;
a first active electrode of conductive material disposed on the distal end of the elongate shaft the first active electrode having an edge feature, and the first active electrode electrically coupled to the first electrical pin;
a first return electrode of conductive material, the first return electrode comprising an extended feature disposed a substantially constant distance from a distal apex of the first active electrode, and the first return electrode electrically coupled to the second electrical pin; and
an aspiration aperture on the distal end of the elongate shaft fluidly coupled to a second fluid conduit, the second fluid conduit within the elongate shaft and wherein the aspiration aperture is offset from a plane that bisects the distal end thickness of the elongate shaft.

2. The electrosurgical wand of claim 1 wherein the edge feature is at least one selected from the group consisting of: a scalloped portion, a cut, a divot, and an asperity.

3. The electrosurgical wand of claim 1 wherein the edge feature comprises a cut, the cut has a diameter and a depth on each side between and including 0.008 and 0.012 inches.

4. The electrosurgical wand of claim 1 wherein the edge feature comprises a cut, the cut has a diameter and a depth on each side of 0.010 inches.

5. The electrosurgical wand of claim 1 wherein the edge feature comprises a first and second cut disposed on opposed sides of the first active electrode.

6. The electrosurgical wand of claim 1 wherein first active electrode further comprises a loop of wire.

7. The electrosurgical wand of claim 6 wherein the loop of wire has a diameter between and including 0.025 and 0.035 inches.

8. The electrosurgical wand of claim 6 wherein the loop of wire has a diameter of 0.030 inches.

9. The electrosurgical wand of claim 1 wherein the non-conductive spacer comprises a step feature operable to limit a tissue penetration depth of the first active electrode.

10. The electrosurgical wand of claim 1 wherein the extended feature comprises a tab.

11. The electrosurgical wand of claim 1 wherein the plurality of discharge apertures are fluidly coupled to a plurality of fluid flow channels disposed in an annular gap between the insulative sheath and the elongate shaft.

12. The electrosurgical wand of claim 1 wherein the plurality of discharge apertures encircle the elongate shaft.

13. The electrosurgical wand of claim 1 wherein the plurality of discharge apertures are spaced proximally from a distal-most tip of the first return electrode.

14. The electrosurgical wand of claim 1 wherein the aspiration aperture defines an aperture width, and wherein a spacer fluid conduit transitions in width from the aperture width to a fluid conduit opening width not less than half an internal diameter of the shaft.

15. The electrosurgical wand of claim 14 wherein the spacer fluid conduit further transitions in depth from an aspiration chamber depth not less than half a thickness of a non-conductive spacer to a fluid conduit opening depth.

16. A system comprising:
an electrosurgical controller, the electrosurgical controller configured to produce radio frequency (RF) energy at an active terminal with respect to a return terminal;
an electrosurgical wand coupled to the electrosurgical controller, the electrosurgical wand comprising:
an elongate shaft that defines a handle end and a distal end;
an insulative sheath characterized by a plurality of discharge apertures on the distal end of the elongate shaft, the plurality of discharge apertures fluidly coupled to a first fluid conduit, and the first fluid conduit within the elongate shaft;
a first active electrode of conductive material disposed on the distal end of the elongate shaft; wherein the first active electrode has an edge feature, and the first active electrode electrically coupled to the first electrical pin;
a first return electrode of conductive material, the first return electrode comprising an extended feature disposed a substantially constant distance from a distal apex of the first active electrode, and the first return electrode electrically coupled to the second electrical pin; and
an aspiration aperture on the distal end of the elongate shaft; the aspiration aperture having an aperture width and fluidly coupled to a spacer fluid conduit, the conduit transitioning in width from the aperture width to a fluid conduit opening width not less than half an internal diameter of the shaft.

17. The electrosurgical wand of claim 16 wherein the edge feature is at least one selected from the group consisting of: a scalloped portion, a cut, a divot, and an asperity.

18. The electrosurgical wand of claim 16 wherein the edge feature comprises a cut, the cut has a diameter and a depth on each side between and including 0.008 and 0.012 inches.

19. The electrosurgical wand of claim 16 wherein the edge feature comprises a cut, the cut has a diameter and a depth on each side of 0.010 inches.

20. The electrosurgical wand of claim 16 wherein first active electrode further comprises a loop of wire.

21. The electrosurgical wand of claim 20 wherein the loop of wire has a diameter between and including 0.025 and 0.035 inches.

22. The electrosurgical wand of claim 20 wherein the loop of wire has a diameter of 0.030 inches.

23. The electrosurgical wand of claim 16 wherein the extended feature comprises a tab.

24. The electrosurgical wand of claim 16 wherein the plurality of discharge apertures are fluidly coupled to a plurality of fluid flow channels disposed in an annular gap between the insulative sheath and the elongate shaft.

25. The electrosurgical wand of claim 16 wherein the plurality of discharge apertures encircle the elongate shaft.

26. The electrosurgical wand of claim 16 wherein the plurality of discharge apertures are spaced proximally from a distal-most tip of the first return electrode.

27. A method comprising:
flowing a conductive fluid within a fluid conduit disposed within a electrosurgical wand, wherein the conductive fluid discharges through a plurality of discharge apertures flows past a return electrode disposed distally from the fluid conduit over an active electrode, and is then aspirated though an aspiration aperture that is offset from a plane that bisects the thickness of the active electrode;
applying electrical energy between the active electrode and the return electrode;
forming, responsive to the energy, a localized plasma proximate to an edge feature disposed on the active electrode;
ablating, by the localized plasma, a portion of a target tissue proximate to the edge feature; and
heating, responsive to the energy, the target tissue proximate to a smooth feature disposed on the active electrode at locations spaced away from the edge feature to thereby provide concomitant hemostasis.

28. The method of claim 27 wherein flowing further comprises flowing the conductive fluid such that the conductive fluid is discharged at least partially toward the active electrode in the form of loop of wire.

29. The method of claim 27 wherein the aspiration aperture is fluidly connected with a fluid conduit in the electrosurgical wand, the aspiration aperture distal to the plurality of discharge apertures.

30. The method of claim 27 wherein the return electrode comprises an extended feature disposed a substantially constant distance from a distal apex of the active electrode.

31. An electrosurgical wand comprising:
an elongate shaft that defines a handle end and a distal end;
a connector comprising first and second electrical pins;
a first active electrode of conductive material disposed on the distal end of the elongate shaft, the first active electrode is electrically coupled to the first electrical pin;
wherein the first active electrode has an edge feature at a first discrete location, and a smooth feature at a second discrete location; and
a first return electrode of conductive material, the first return electrode electrically coupled to the second electrical pin; and
an aspiration aperture on the distal end of the elongate shaft, defining an aspiration aperture width and wherein the aspiration aperture is fluidly connected with a spacer fluid conduit, the conduit transitioning in width from the aperture width to a fluid conduit opening width that is not less than half an internal diameter of the shaft.

32. The electrosurgical wand of claim 31, wherein the edge feature is operable to ablate tissue, and wherein the smooth feature is operable to heat tissue for concomitant hemostasis.

33. The electrosurgical wand of claim 31, wherein the aspiration aperture is located on only one side of the elongate shaft and is disposed on an inferior surface of a non-conductive spacer supporting the first active electrode.

34. An electrosurgical wand comprising:
an elongate shaft that defines a handle end and a distal end;
a connector comprising first and second electrical pins;
an insulative sheath characterized by a plurality of discharge apertures on the distal end of the elongate shaft, the plurality of discharge apertures fluidly coupled to a first fluid conduit, and the first fluid conduit within the elongate shaft;
a first active electrode of conductive material disposed on the distal end of the elongate shaft, the first active electrode electrically coupled to the first electrical pin, and having an edge feature;
a non-conductive spacer disposed adjacent the first active electrode, the spacer comprising a step feature operable to limit the tissue penetration depth of the first active electrode;
a first return electrode of conductive material, the first return electrode comprising an extended feature disposed a substantially constant distance from a distal apex of the first active electrode, and the first return electrode electrically coupled to the second electrical pin; and
an aspiration aperture on the distal end of the elongate shaft fluidly coupled to a second fluid conduit, the second fluid conduit within the elongate shaft.

35. An electrosurgical wand comprising:
an elongate shaft that defines a handle end and a distal end;
a connector comprising a first and second electrical pins;
an insulative sheath characterized by a plurality of discharge apertures on the distal end of the elongate shaft, the plurality of discharge apertures fluidly coupled to a first fluid conduit, and the first fluid conduit within the elongate shaft;
a first active electrode of conductive material disposed on the distal end of the elongate shaft, the first active electrode electrically coupled to the first electrical pin and including an edge feature;
a first return electrode of conductive material, the first return electrode comprising an extended feature disposed a substantially constant distance from a distal apex of the first active electrode, and the first return electrode electrically coupled to the second electrical pin; and
an aspiration aperture on the distal end of the elongate shaft fluidly coupled to a second fluid conduit, the second fluid conduit within the elongate shaft; and wherein the aspiration aperture defines an aperture width, and wherein a spacer fluid conduit transitions in width from the aperture width to a fluid conduit opening width not less than half an internal diameter of the shaft.

36. The electrosurgical wand of claim 35 wherein the spacer fluid conduit further transitions in depth from an aspiration chamber depth not less than half a thickness of a non-conductive spacer to a fluid conduit opening depth.

37. A system comprising:
an electrosurgical controller, the electrosurgical controller configured to produce radio frequency (RF) energy at an active terminal with respect to a return terminal;
an electrosurgical wand coupled to the electrosurgical controller, the electrosurgical wand comprising:
an elongate shaft that defines a handle end and a distal end;
an insulative sheath characterized by a plurality of discharge apertures on the distal end of the elongate shaft, the plurality of discharge apertures fluidly coupled to a first fluid conduit, and the first fluid conduit within the elongate shaft;

a first active electrode of conductive material disposed on the distal end of the elongate shaft, the first active electrode electrically coupled to the first electrical pin and including an edge feature;

a first return electrode of conductive material, the first return electrode comprising an extended feature disposed a substantially constant distance from a distal apex of the first active electrode, and the first return electrode electrically coupled to the second electrical pin; and an aspiration aperture on the distal end of the elongate shaft fluidly coupled to a second fluid conduit, the second fluid conduit within the elongate shaft and wherein the aspiration aperture is offset from a plane that bisects the thickness of the distal end of the elongate shaft.

* * * * *